US008642628B2

(12) United States Patent
Wasley et al.

(10) Patent No.: US 8,642,628 B2
(45) Date of Patent: Feb. 4, 2014

(54) PYRROLE INHIBITORS OF S-NITROSOGLUTATHIONE REDUCTASE

(75) Inventors: Jan Wasley, Guilford, CT (US); Gary J. Rosenthal, Lafayette, CO (US); Xicheng Sun, Broomfield, CO (US); Sarah Strong, Louisville, CO (US); Jian Qiu, Longmont, CO (US)

(73) Assignee: N30 Pharmaceuticals, Inc., Boulder, CO (US)

( * ) Notice: Subject to any disclaimer, the term of this patent is extended or adjusted under 35 U.S.C. 154(b) by 437 days.

(21) Appl. No.: 13/057,175

(22) PCT Filed: Aug. 14, 2009

(86) PCT No.: PCT/US2009/053929
§ 371 (c)(1),
(2), (4) Date: Feb. 2, 2011

(87) PCT Pub. No.: WO2010/019909
PCT Pub. Date: Feb. 18, 2010

(65) Prior Publication Data
US 2011/0136875 A1    Jun. 9, 2011

Related U.S. Application Data

(60) Provisional application No. 61/089,313, filed on Aug. 15, 2008.

(51) Int. Cl.
*A61K 31/4178*    (2006.01)
*A61K 31/40*    (2006.01)
*A61K 31/4439*    (2006.01)
*C07D 401/04*    (2006.01)
*C07D 403/10*    (2006.01)
*C07D 207/333*    (2006.01)

(52) U.S. Cl.
USPC ........ 514/343; 514/397; 514/427; 548/314.7; 548/561; 546/276.4

(58) Field of Classification Search
None
See application file for complete search history.

(56) References Cited

U.S. PATENT DOCUMENTS

| 3,168,527 A | 2/1965 | Short |
|---|---|---|
| 3,168,528 A | 2/1965 | Short |
| 3,168,529 A | 2/1965 | Short |
| 3,168,531 A | 2/1965 | Short |
| 3,168,532 A | 2/1965 | Short |
| 3,427,305 A | 2/1969 | Chinn |
| 3,752,826 A | 8/1973 | Carson et al. |
| 4,694,018 A | 9/1987 | Chinn |
| 4,792,568 A | 12/1988 | Auerbach |
| 4,826,869 A | 5/1989 | Muchowski et al. |
| 5,189,051 A | 2/1993 | Smith |
| 5,236,943 A | 8/1993 | Heitsch et al. |
| 5,451,597 A | 9/1995 | Bovy et al. |
| 5,789,440 A | 8/1998 | Ellsworth et al. |
| 5,935,990 A | 8/1999 | Khanna et al. |
| 6,008,368 A | 12/1999 | Bovy et al. |
| 6,355,812 B1 | 3/2002 | Ferro et al. |
| 6,391,064 B1 | 5/2002 | Baudry et al. |
| 6,451,833 B1 | 9/2002 | Bovy et al. |
| 6,590,119 B2 | 7/2003 | Ferro et al. |
| 6,809,117 B2 | 10/2004 | Enikolopov et al. |
| 7,186,716 B2 | 3/2007 | Wei et al. |
| 7,223,791 B2 | 5/2007 | Maekawa et al. |
| 8,470,857 B2 | 6/2013 | Wasley et al. |
| 2002/0107408 A1 | 8/2002 | Ferro et al. |
| 2002/0128205 A1 | 9/2002 | Stamler et al. |
| 2005/0014697 A1 | 1/2005 | Stamler et al. |
| 2005/0187166 A1 | 8/2005 | Stamler et al. |
| 2005/0215613 A1 | 9/2005 | Teng et al. |
| 2005/0282843 A1 | 12/2005 | Wang et al. |
| 2006/0148798 A1 | 7/2006 | Lundstedt et al. |
| 2006/0270628 A1 | 11/2006 | Das et al. |
| 2006/0293320 A1 | 12/2006 | Schmistz et al. |
| 2007/0082912 A1 | 4/2007 | Giblin et al. |
| 2008/0045542 A1 | 2/2008 | Ronan et al. |
| 2008/0114022 A1 | 5/2008 | Bala et al. |
| 2010/0286174 A1 | 11/2010 | Stamler et al. |
| 2011/0136881 A1 | 6/2011 | Wasley et al. |
| 2011/0144110 A1 | 6/2011 | Wasley et al. |
| 2011/0144180 A1 | 6/2011 | Wasley et al. |
| 2012/0245210 A1 | 9/2012 | Sun |

FOREIGN PATENT DOCUMENTS

| CN | 101006052 A | 7/2007 |
|---|---|---|
| FR | 1393615 | 3/1965 |
| GB | 1029915 | 6/1962 |
| GB | 997043 | 6/1963 |
| JP | 39012632 | 7/1964 |
| JP | 2006290791 | 10/2006 |
| WO | WO 2005/000229 | 1/2005 |
| WO | WO 2006/012642 | 2/2006 |
| WO | WO 2006/133926 | 12/2006 |
| WO | WO 2007/009083 | 1/2007 |
| WO | WO 2009/076665 | 6/2009 |
| WO | WO 2010/019903 | 2/2010 |

(Continued)

OTHER PUBLICATIONS

European Search Opinion issued Jul. 22, 2011 in EP application serial No. 09807382.8.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
European Search Opinion issued Sep. 23, 2011 in EP application serial No. 09807379.4.
European Search Opinion issued Nov. 29, 2011 in EP application serial No. 09807378.6.
European Search Opinion issued Dec. 4, 2012 in EP application serial No. 09807383.6.

(Continued)

*Primary Examiner* — Michael Barker
(74) *Attorney, Agent, or Firm* — Swanson & Bratschun, L.L.C.

(57) ABSTRACT

The present invention is directed to inhibitors of S-nitrosoglutathione reductase (GSNOR), pharmaceutical compositions comprising such GSNOR inhibitors, and methods of making and using the same.

8 Claims, No Drawings

(56) References Cited

FOREIGN PATENT DOCUMENTS

| WO | WO 2010/019905 | 2/2010 |
|---|---|---|
| WO | WO 2010/019909 | 2/2010 |
| WO | WO 2010/019910 | 2/2010 |
| WO | WO 2010/107476 | 9/2010 |

OTHER PUBLICATIONS de Belder et al. (May 1994) "Effects of S-nitroso-glutathione in the human forearm circulation; evidence for selective inhibition of platelet activation", *Cardiovasc Res.*, 28(5):691-694.

de Jesus-Berrios et al. (Nov. 2003) "Enzymes that Counteract Nitrosative Stress Promot Fungal Virulence", *Curr. Biol.*, 13:1963-1968.

Foster et al. (Apr. 2003) "S-nitrosylation in health and disease", *Trends in Molecular Medicine*, 9(4):160-168.

Gaston et al. (Dec. 1993) "Endogenous nitrogen oxides and bronchodilator S-nitrosolthiols in human airways", *Proc. Natl. Acad. Sci. USA*, 90:10957-10961.

International Preliminary Report on Patentability issued in PCT/US2009/053923 mailed Feb. 24, 2011.

International Preliminary Report on Patentability issued in PCT/US2009/053925 mailed Feb. 24, 2011.

International Preliminary Report on Patentability issued in PCT/US2009/053929 mailed Feb. 24, 2011.

International Preliminary Report on Patentability issued in PCT/US2009/053931 mailed Feb. 24, 2011.

International Search Report and Written Opinion issued in PCT/US2009/053923 mailed Oct. 15, 2009.

International Search Report and Written Opinion issued in PCT/US2009/053925 mailed Oct. 15, 2009.

International Search Report and Written Opinion issued in PCT/US2009/053929 mailed Oct. 15, 2009.

International Search Report and Written Opinion issued in PCT/US2009/053931 mailed Oct. 9, 2009.

Jensen et al. (1998) "S-Nitrosoglutathione is a substrate for rat alcohol dehydrognease class III isoenzyme", *Biochem J.*, 331:659-668.

Kaposzta et al. (2002) "S-Nitrosoglutathione Reduces Asymptomatic Embolization After Carotid Angioplasty", *Circulation*, 106(24):3057-3062.

Kauffman et al. (2001) "QSAR and k-Nearest Neighbor Classification Analysis of Selective Cyclooxygenase-2 Inhibitors Using Topologically-Based Numerical Descriptors", *J. Chem. Inf. Comput. Sci*, 41(6):1553-1560.

Khanna et al. (1997) "1,2-Diarylpyrroles as Potent and Selective Inhibitors of Cyclooxygenase-2", *J. Med. Chem*, 40 (11):1619-1633.

Lipton et al. (Sep. 2001) "S-Nitrosothiols signal the ventilatory response to hypoxia", *Nature*, 413:171-174.

Liu et al. (Feb. 2004) "Essential Roles of S-Nitrosothiols in Vascular Homeostatsis and Endotoxic Shock", *Cell*, 116(4):617-628.

Liu et al. (Mar. 2001) "A metabolic enzyme for S-nitrosothiol conserved from bacterial to humans", *Nature*, 410:490-494.

Que et al. (Jun. 2005) "Protection from Experimental Asthma by an Endogenous Bronchodilator", *Science*, 308(5728):1618-1621.

Sanghani et al. (2000) "Kinetic Mechanism of Human Glutathioone-Dependent Formaldehyde Dehydrogenase", *Biochemistry*, 39:10720-10729.

Sanghani et al. (2002) "Human Glutathione-Dependent Formaldehyde Dehydrognease. Structures of Apo, Binary, and Inhibitory Ternary Complexes", *Biochemistry*, 41:10778-10786.

Schepetkin et al. (2006) "Novel Small-Molecule Inhibitors of Anthrax Lethal Factor Identified by High-Throughput Screening", *Journal of Medicinal Chemistry*, 49(17):5232-5244.

Stabb et al. (2008) "Dual functions of alcohol dehydrogenase 3: implications with focus on formaldehyde dehydrogenase and S-nitroglutathione reductase activities", *Cell Mol. Life Sci*, 65:3950-3960.

Stamler et al. (Aug. 1992) "Nitric oxide circulates in mammalian plasma primarily as an S-nitrose adduct of serium albumin", *Proc. Natl. Acad. Sci. USA*, 89:7674-7677.

Uotila and Koivusalo (1989) Coenzymes and Cofactors vol. 3: Glutathione, part A., D. Dolphin, ed. pp. 517-551 (New York, John Wiley & Sons).

Zaman et al. (2001) "S-Nitrosoglutathione Increases Cystic Fibrosis Transmembrane Regulator Maturation", *Biochem Biophys Res Commun.*, 284:65-70.

Patani et al. (1996) Chem. Rev. 96:3147-3176, "Bioisosterism: A Rational Approach in Drug Design".

International Preliminary Report on Patentability issued in PCT/US2010/060303 mailed Jun. 28, 2012.

International Search Report and Written Opinion issued Sep. 26, 2012 in PCT application serial No. PCT/US2012/045434.

US 8,642,628 B2

PYRROLE INHIBITORS OF S-NITROSOGLUTATHIONE REDUCTASE

RELATED APPLICATIONS

This application is a 35 U.S.C. §371 national phase application of PCT/US2009/053929, filed Aug. 14, 2009 (WO 2010/019909), entitled "Pyrrole Inhibitors of S-Nitrosoglutathione Reductase," which claims priority to U.S. Provisional Application Ser. No. 61/089,313, filed Aug. 15, 2008, which is incorporated herein by reference in its entirety.

FIELD OF THE INVENTION

The present invention is directed to novel pyrrole inhibitors of S-nitrosoglutathione reductase, pharmaceutical compositions comprising such inhibitors, and methods of making and using the same.

BACKGROUND OF THE INVENTION

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA,* 89:7674-7677 (1992)). Protein SNO's play broad roles in cardiovascular, respiratory, metabolic, gastrointestinal, immune and central nervous system function (Foster et al., 2003, Trends in Molecular Medicine Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., 2001) within cells. Given this pivotal position in the NO-SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.,* 331:659-668 (1998); Liu et al., *Nature,* 410:490-494 (2001)). GSNOR is also known as glutathione-dependent formaldehyde dehydrogenase (GS-FDH), alcohol dehydrogenase 3 (ADH-3) (Uotila and Koivusalo, *Coenzymes and Cofactors.,* D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature,* 413:171-174 (2001)) to regulation of the cystic fibrosis transmembrane regulator (Zaman et al., *Biochem Biophys Res Commun,* 284: 65-70 (2001), to regulation of vascular tone, thrombosis and platelet function (de Belder et al., Cardiovasc Res. 1994 May; 28(5):691-4. (1994); Z. Kaposzta, A et al., Circulation; 106 (24): 3057-3062, 2002) as well as host defense (de Jesus-Berrios et al., *Curr. Biol.,* 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNOR as a primary physiological ligand for the enzyme S-nitrosoglutathione reductase (GSNOR), which catabolizes GSNO and consequently reduces available SNO's and NO in biological systems (Liu et al., 2001), (Liu et al., Cell, (2004), 116(4), 617-628), and (Que et al., Science, 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to increased NO synthesis and/or increased NO bioactivity. In addition, there is a significant need for novel compounds, compositions and methods for preventing, ameliorating, or reversing other NO-associated disorders. The present invention satisfies these needs.

SUMMARY OF THE INVENTION

The present invention provides novel pyrrole compounds useful as S-nitrosoglutathione reductase ("GSNOR") inhibitors. The invention encompasses pharmaceutically acceptable salts, prodrugs, and metabolites of the described GSNOR inhibitors. Also encompassed by the invention are pharmaceutical compositions comprising at least one GSNOR inhibitor and at least one pharmaceutically acceptable carrier.

The compositions of the present invention can be prepared in any suitable pharmaceutically acceptable dosage form.

The present invention provides a method for inhibiting S-nitrosoglutathione reductase in a subject in need thereof. Such a method comprises administering a therapeutically effective amount of a pharmaceutical composition comprising at least one GSNOR inhibitor or a pharmaceutically acceptable salt thereof, a prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION OF THE PREFERRED EMBODIMENTS

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants and animals and is well conserved. The proteins from *E. coli, S. cerevisiae* and mouse macrophages share over 60% amino acid sequence identity. GSNOR activity (i.e., decomposition of S-nitrosoglutathione when NADH is present as a required cofactor) has been detected in *E. coli*, in mouse macrophages, in mouse endothelial cells, in mouse smooth muscle cells, in yeasts, and in human HeLa, epithelial and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in all diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted pyrrole analogs that are inhibitors of GSNOR having the structures depicted below (Formula I), or a pharmaceutically acceptable salt, stereoisomer, or prodrug thereof.

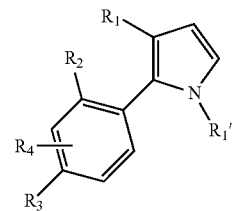

Tri-substituted pyrrole analogs are potent inhibitors of GSNOR. As used in this context, the term "analog" refers to a compound having similar chemical structure and function as compounds of Formula I that retains the pyrrole ring.

Some pyrrole analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

In accordance with the invention, the levels of the S-nitrosoglutathione reductase in the biological sample can be determined by the methods described in U.S. Patent Application Publication No. 2005/0014697. The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells.

B. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —$N(R^c)_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" or "carboxy" or "carboxyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl" as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl" by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, and —CH$_2$—CH=N—OCH$_3$. Up to two heteroatoms can be consecutive, such as, for example, —CH$_2$—NH—OCH$_3$. When a prefix such as (C$_2$-C$_8$) is used to refer to a heteroalkyl group, the number of carbons (2 to 8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH.

To further illustrate the definition of a heteroalkyl group, where the heteroatom is oxygen, a heteroalkyl group can be an oxyalkyl group. For instance, (C2-C5) oxyalkyl is meant to include, for example —CH$_2$—O—CH$_3$ (a C$_3$-oxyalkyl group with two carbon atoms and one oxygen replacing a carbon atom), —CH$_2$CH$_2$CH$_2$CH$_2$OH, —OCH$_2$CH$_2$OCH$_2$CH$_2$OH, —OCH$_2$CH(OH)CH$_2$OH, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl" by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl" as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$ CH$_2$CH$_2$CH$_2$OH, —CH$_2$CH$_2$CH$_2$CH$_2$CH$_2$OH, and branched versions thereof.

The term "hydroxy" or "hydroxyl" includes groups with an —OH or —O$^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO$^+$) and nitroxyl ion (NO$^-$). The reactive form of nitric oxide can be provided by gaseous nitric oxide. Compounds having the structure X—NO$_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a GSNOR inhibitor is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including —$OR^d$, =O, =$NR^{d\prime}$, =N—$OR^d$, —$NR^{d\prime}R^{d\prime\prime}$, —$SR^{d\prime}$, -halo, —$SiR^{d\prime}R^{d\prime\prime}R^{d\prime\prime\prime}$, —$OC(O)R^{d\prime}$, —$C(O)R^{d\prime}$, —$CO_2R^{d\prime}$, —$CONR^{d\prime}R^{d\prime\prime}$, —$OC(O)NR^{d\prime}R^{d\prime\prime}$, —$NR^{d\prime\prime}C(O)R^{d\prime}$, —$NR^{d\prime\prime\prime}C(O)NR^{d\prime}R^{d\prime\prime}$, —$NR^{d\prime\prime\prime}SO_2NR^{d\prime}R^{d\prime\prime}$, —$NR^{d\prime\prime}CO_2R^{d\prime}$, —$NHC(NH_2)$=NH, —$NR^{a\prime}C(NH_2)$=NH, —$NHC(NH_2)$=$NR^{d\prime}$, —$S(O)R^{d\prime}$, —$SO_2R^{d\prime}$, —$SO_2NR^{d\prime}R^{d\prime\prime}$, —$NR^{d\prime\prime}SO_2R^{d\prime}$, —CN and —$NO_2$, in a number ranging from zero to three, with those groups having zero, one or two substituents being exemplary.

$R^{d\prime}$, $R^{d\prime\prime}$ and $R^{d\prime\prime\prime}$ each independently refer to hydrogen, unsubstituted ($C_1$-$C_8$)alkyl, unsubstituted hetero($C_1$-$C_8$) alkyl, unsubstituted aryl and aryl substituted with one to three substituents selected from -halo, unsubstituted alkyl, unsubstituted alkoxy, unsubstituted thioalkoxy and unsubstituted aryl ($C_1$-$C_4$)alkyl. When $R^{d\prime}$ and $R^{d\prime\prime}$ are attached to the same nitrogen atom, they can be combined with the nitrogen atom to form a 5-, 6- or 7-membered ring. For example, —$NR^{d\prime}R^{d\prime\prime}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to —$OR^{d\prime}$, =O, =$NR^{d\prime}$, =N—$OR^{d\prime}$, —$NR^{d\prime}R^{d\prime\prime}$, —$SR^{d\prime}$, -halo, —$SiR^{d\prime}R^{d\prime\prime}R^{d\prime\prime\prime}$, —$OC(O)R^{d\prime}$, —$C(O)R^{d\prime}$, —$CO_2R^{d\prime}$, —$CONR^{d\prime}R^{d\prime\prime}$, —$OC(O)NR^{d\prime}R^{d\prime\prime}$, —$NR^{d\prime\prime}C(O)R^{d\prime}$, —$NR^{d\prime\prime\prime}C(O)NR^{d\prime}R^{d\prime\prime}$, —$NR^{d\prime\prime}SO_2NR^{d\prime}R^{d\prime\prime}$, —$NR^{d\prime\prime}CO_2R^{d\prime}$, —$NHC(NH_2)$=NH, —$NR^{a\prime}C(NH_2)$=NH, —$NHC(NH_2)$=$NR^d$, —$S(O)_R{^{d\prime}}$, —$SO_2R^d$, —$SO_2NR^{d\prime}R^{d\prime\prime}$, —$NR^{d\prime\prime}SO_2R^d$, —CN and —$NO_2$, where $R^{d\prime}$, $R^{d\prime\prime}$ and $R^{d\prime\prime\prime}$ are as defined above. Typical substituents can be selected from: —$OR^{d\prime}$, =O, —$NR^{d\prime}R^{d\prime\prime}$, -halo, —$OC(O)R^{d\prime}$, —$CO_2R^{d\prime}$, —$C(O)NR^{d\prime}R^{d\prime\prime}$, —$OC(O)NR^{d\prime}R^{d\prime\prime}$, —$NR^{d\prime\prime}C(O)R^{d\prime}$, —$NR^{d\prime\prime}CO_2R^{d\prime}$, —$NR^{d\prime\prime\prime}SO_2NR^{d\prime}R^{d\prime\prime}$, —$SO_2R^{d\prime}$, —$SO_2NR^{d\prime}R^{d\prime\prime}$, —$NR^{d\prime\prime}SO_2R^{d\prime}$, —CN and —$NO_2$.

Similarly, substituents for the aryl and heteroaryl groups are varied and selected from: -halo, —$OR^{e\prime}$, —$OC(O)R^{e\prime}$, —$NR^{e\prime}R^{e\prime\prime}$, —$SR^{e\prime}$, —$R^{e\prime}$, —CN, —$NO_2$, —$CO_2R^{e\prime}$, —$C(O)NR^{e\prime}R^{e\prime\prime}$, —$C(O)R^{e\prime}$, —$OC(O)NR^{e\prime}R^{e\prime\prime}$, —$NR^{e\prime\prime}C(O)R^{e\prime}$, —$NR^{e\prime\prime}CO_2R^{e\prime}$, —$NR^{e\prime\prime\prime}C(O)NR^{e\prime}R^{e\prime\prime}$, —$NR^{e\prime\prime\prime}SO_2NR^{e\prime}R^{e\prime\prime}$, —$NHC(NH_2)$=NH, —$NR^{e\prime}C(NH_2)$=NH, —NH—$C(NH_2)$=$NR^{e\prime}$, —$S(O)R^{e\prime}$, —$SO_2R^{e\prime}$, —$SO_2NR^{e\prime}R^{e\prime\prime}$, —$NR^{e\prime\prime}SO_2R^{e\prime}$, —$N_3$, —$CH(Ph)_2$, perfluoroalkoxy and perfluoro($C_1$-$C_4$)alkyl, in a number ranging from zero to the total number of open valences on the aromatic ring system.

$R^{e\prime}$, $R^{e\prime\prime}$ and $R^{e\prime\prime\prime}$ are independently selected from hydrogen, unsubstituted ($C_1$-$C_8$) alkyl, unsubstituted hetero($C_1$-$C_8$) alkyl, unsubstituted aryl, unsubstituted heteroaryl, unsubstituted aryl($C_1$-$C_4$) alkyl and unsubstituted aryloxy ($C_1$-$C_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -J-$(CH_2)_r$—K—, wherein J and K are independently —$CH_2$—, —O—, —NH—, —S—, —S(O)—, —$S(O)_2$—, —$S(O)_2NR^{f\prime}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —$NR^{f\prime}$—, —S—, —S(O)—, —$S(O)_2$—, or —$S(O)_2NR^{a\prime}$—. The substituent $R^{f\prime}$ in —$NR^{f\prime}$ and —$S(O)_2NR^{f\prime}$— is selected from hydrogen or unsubstituted ($C_1$-$C_6$)alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

C. S-Nitrosoglutathione Reductase Inhibitors
1. Inventive Compounds

In one of its aspects the present invention provides a compound having a structure shown in Formula I, or a pharmaceutically acceptable salt, stereoisomer, or prodrug thereof:

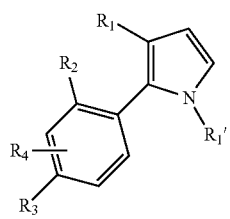

I wherein
$R_1$ is selected from the group consisting $R_5$ or $R_6$;
$R_1'$ is $R_5$ when $R_1$ is $R_6$, and $R_6$ when $R_1$ is $R_5$;
$R_2$ is selected from the group consisting of hydrogen, halogen, hydroxyl, $C_1$-$C_6$ alkyl, $C_3$-$C_6$ cycloalkyl, cyano, nitro, $CF_3$, carbamoyl, $C_1$-$C_6$ alkylcarbamoyl, amino, $C_1$-$C_6$ alkylamino, $C_1$-$C_6$ dialkylamino, $C_1$-$C_6$ alkoxyl, and $C_3$-$C_6$ cycloalkoxyl;
$R_3$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, amino, trifluoromethyl, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, aryl, substituted aryl, heteroaryl, and substituted heteroaryl;
$R_4$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkyl sulfamoyl, amino, $C_1$-$C_6$ alkylamino, $C_1$-$C_6$ dialkylamino, $C_1$-$C_6$ alkoxyl, and $C_3$-$C_6$ cycloalkoxyl;
$R_5$ is selected from the group consisting of aryl, substituted aryl, heteroaryl, or substituted heteroaryl;
$R_6$ is selected from the group consisting of —$CR_7R_8CR_9R_{10}$ $(CR_{11}R_{12})_nR_{13}$ and

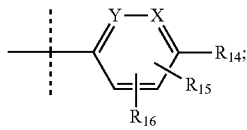

$R_7$, $R_8$, $R_9$, $R_{10}$, $R_{11}$, and $R_{12}$ are each independently selected from hydrogen, hydroxyl, halogen, $C_1$-$C_6$ alkyl, $C_3$-$C_6$ cycloalkyl, aryl, substituted aryl, heteroaryl, substituted heteroaryl and wherein $R_9$ and $R_{10}$ together form a $C_3$-$C_6$ cycloalkyl;
$R_{13}$ is selected from the group consisting of COOH and $NH_2SO_2CF_3$;
$R_{14}$ is selected from the group consisting of OH, COOH, and $SO_2NH_2$;
$R_{15}$ and $R_{16}$ are independently selected from the group consisting of hydrogen, hydroxyl, carboxyl, $NO_2$, halogen, cyano, and carbamoyl;
n is 0 or 1; and
X and Y are independently selected from the group consisting of C and N.

In a further aspect of the invention, suitable identities for $R_5$ include, but are not limited to, 4-chlorophenyl, 3-chlorophenyl, 4-chloro-2-methoxyphenyl, 4-bromophenyl, 3-bromophenyl, 4-fluorophenyl, 3-fluorophenyl, 4-hydroxyphenyl, 4-methoxyphenyl, 3-methoxyphenyl, 2-methoxyphenyl, 4-chlorothiophen-2-yl, 5-chlorothiophen-2-yl, 3-bromothiophen-2-yl, 4-bromothiophen-2-yl, 5-bromothiopheny-2-yl, 5-bromothiophen-3-yl, and

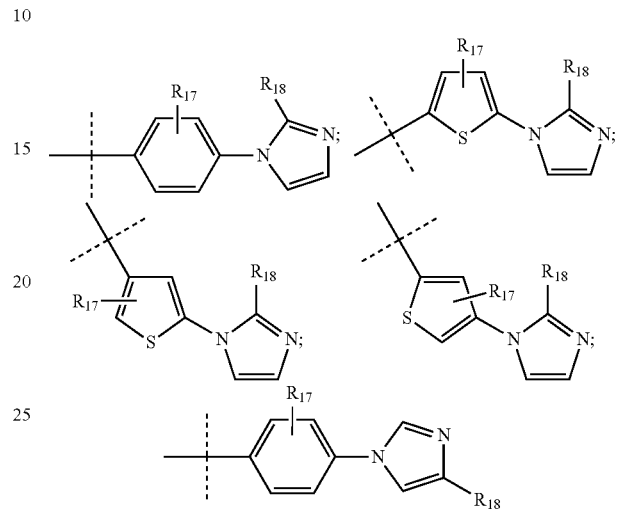

wherein
$R_{17}$ is selected from the group consisting of hydrogen, methyl, chloro, fluoro, hydroxy, methoxy, ethoxy, propoxy, carbamoyl, dimethylamino, amino, formamido, and trifluoromethyl; and
$R_{18}$ is selected from the group consisting of hydrogen, methyl, and ethyl.

In a further aspect of the invention, suitable identities for $R_2$ include, but are not limited to, $C_1$-$C_6$ alkyl, suitable identity for $R_3$ includes, but is not limited to carbamoyl, and suitable identity for $R_4$ includes, but is not limited to hydrogen.

In a further aspect of the invention, suitable identities for $R_5$ include, but are not limited to, 4-methoxyphenyl, 4-chloro-2-methoxyphenyl, 4-(1H-imidazol-1-yl)phenyl, 4-(2-methyl-1H-imidazol-1-yl)phenyl.

In a further aspect of the invention, suitable compounds of formula I include, but are not limited to:
3-(2-(4-carbamoyl-2-methylphenyl)-3-(4-methoxyphenyl)-1H-pyrrol-1-yl)propanoic acid;
3-(2-(4-carbamoyl-2-methylphenyl)-3-(4-methoxyphenyl)-1H-pyrrol-1-yl)-3-phenylpropanoic acid;
3-(2-(4-carbamoyl-2-methylphenyl)-3-(4-methoxyphenyl)-1H-pyrrol-1-yl)-2-methylpropanoic acid;
4-(2-(4-carbamoyl-2-methylphenyl)-3-(4-methoxyphenyl)-1H-pyrrol-1-yl)butanoic acid;
3-(3-(4-(1H-imidazol-1-yl)phenyl)-2-(4-carbamoyl-2-methylphenyl)-1H-pyrrol-1-yl)propanoic acid;
3-(2-(4-carbamoyl-2-methylphenyl)-1-(4-methoxyphenyl)-1H-pyrrol-3-yl)propanoic acid;
3-(2-(4-carbamoyl-2-methylphenyl)-3-(4-methoxyphenyl)-1H-pyrrol-1-yl)butanoic acid;
1-((2-(4-carbamoyl-2-methylphenyl)-3-(4-methoxyphenyl)-1H-pyrrol-1-yl)methyl)cyclopropanecarboxylic acid;
3-(2-(4-carbamoyl-2-methylphenyl)-3-(4-methoxyphenyl)-1H-pyrrol-1-yl)-2,2-difluoropropanoic acid;

3-(2-(4-carbamoyl-2-methylphenyl)-3-(4-methoxyphenyl)-1H-pyrrol-1-yl)-2-hydroxypropanoic acid;
3-(2-(4-carbamoyl-2-methylphenyl)-3-(4-methoxyphenyl)-1H-pyrrol-1-yl)hexanoic acid;
—3-(2-(4-carbamoyl-2-methylphenyl)-3-(4-methoxyphenyl)-1H-pyrrol-1-yl)-4-methylpentanoic acid;
3-(1-(4-(1H-imidazol-1-yl)phenyl)-2-(4-carbamoyl-2-methylphenyl)-1H-pyrrol-3-yl)propanoic acid;
3-(2-(4-carbamoyl-2-methylphenyl)-1-(4-chloro-2-methoxyphenyl)-1H-pyrrol-3-yl)propanoic acid;
4-(2-(4-carbamoyl-2-methylphenyl)-3-(4-methoxyphenyl)-1H-pyrrol-1-yl)-2-hydroxybenzoic acid;
4-(2-(4-carbamoyl-2-methylphenyl)-3-(4-methoxyphenyl)-1H-pyrrol-1-yl)-2-fluorobenzoic acid;
4-(1-(4-hydroxy-3-nitrophenyl)-3-(4-methoxyphenyl)-1H-pyrrol-2-yl)-3-methylbenzamide;
4-(1-(6-hydroxypyridin-3-yl)-3-(4-methoxyphenyl)-1H-pyrrol-2-yl)-3-methylbenzamide;
4-(2-(4-carbamoyl-2-methylphenyl)-3-(4-methoxyphenyl)-1H-pyrrol-1-yl)benzoic acid;
4-(2-(4-carbamoyl-2-methylphenyl)-3-(4-methoxyphenyl)-1H-pyrrol-1-yl)-2-chlorobenzoic acid;
4-(3-(4-methoxyphenyl)-1-(2-(trifluoromethylsulfonamido)ethyl)-1H-pyrrol-2-yl)-3-methylbenzamide;
4-(3-(4-methoxyphenyl)-1-(4-sulfamoylphenyl)-1H-pyrrol-2-yl)-3-methylbenzamide;
4-(1-(3-fluoro-4-hydroxyphenyl)-3-(4-methoxyphenyl)-1H-pyrrol-2-yl)-3-methylbenzamide;
5-(2-(4-carbamoyl-2-methylphenyl)-3-(4-methoxyphenyl)-1H-pyrrol-1-yl)picolinic acid;
4-(1-(3,5-difluoro-4-hydroxyphenyl)-3-(4-methoxyphenyl)-1H-pyrrol-2-yl)-3-methylbenzamide;
4-(1-(5-hydroxypyridin-2-yl)-3-(4-methoxyphenyl)-1H-pyrrol-2-yl)-3-methylbenzamide;
5-(2-(4-carbamoyl-2-methylphenyl)-3-(4-methoxyphenyl)-1H-pyrrol-1-yl)-2-hydroxybenzoic acid;
6-(2-(4-carbamoyl-2-methylphenyl)-3-(4-methoxyphenyl)-1H-pyrrol-1-yl)nicotinic acid;
4-(1-(3-fluoro-4-hydroxyphenyl)-3-(4-(2-methyl-1H-imidazol-1-yl)phenyl)-1H-pyrrol-2-yl)-3-methylbenzamide; and
4-(1-(3,5-difluoro-4-hydroxyphenyl)-3-(4-(2-methyl-1H-imidazol-1-yl)phenyl)-1H-pyrrol-2-yl)-3-methylbenzamide.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative GSNOR Inhibitors

Examples 1-30 list representative novel pyrrole analogs of Formula I useful as GSNOR inhibitors of the invention. The synthetic methods that can be used to prepare each compound are detailed in Examples 1-30, with reference to synthetic schemes and intermediates described in Example 31. Supporting mass spectrometry data and proton NMR data for each compound is also included in Examples 1-30. GSNOR inhibitor activity was determined by the assay described in Example 32 and $IC_{50}$ values were obtained. GSNOR inhibitor compounds in Examples 1-30 had an $IC_{50}$ of about <100 µM. GSNOR inhibitor compounds Examples 1, 3, 5, 6, 9, 13-17, 19-20, 23, 25-27, 29-30 had an $IC_{50}$ of about <5 µM. GSNOR inhibitor compounds Examples 1, 5-6, 13-15, 17, 19, 23, 25, 27, 29-30 had an $IC_{50}$ of about less than 1.0 µM.

D. Pharmaceutical Compositions Comprising a GSNOR Inhibitor

The invention encompasses pharmaceutical compositions comprising at least one GSNOR inhibitor described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-GSNOR inhibitor active agents.

The pharmaceutical compositions of the invention can comprise novel GSNOR inhibitors described herein, the pharmaceutical compositions can comprise known compounds which previously were not know to have GSNOR inhibitor activity, or a combination thereof.

The GSNOR inhibitors can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the GSNOR inhibitors described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., GSNOR inhibitor) in the required amount in an appropriate solvent with one or a combination of ingredients enumerated above, as required, followed by filtered sterilization. Generally, dispersions are prepared by incorporating at least one GSNOR inhibitor into a sterile vehicle that contains a basic dispersion medium and any other required ingredients. In the case of sterile powders for the preparation of sterile injectable solutions, exemplary methods of preparation include vacuum drying and freeze-drying, both of which yield a powder of the GSNOR inhibitor plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the GSNOR inhibitor can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the GSNOR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the GSNOR inhibitors may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of GSNOR inhibitor calculated to produce the desired therapeutic effect in association with the required pharmaceutical carrier. The specification for the dosage unit forms of the invention are dictated by and directly dependent on the unique characteristics of the GSNOR inhibitor and the particular therapeutic effect to be achieved, and the limitations inherent in the art of compounding such an active agent for the treatment of individuals.

Pharmaceutical compositions according to the invention comprising at least one GSNOR inhibitor can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one GSNOR inhibitor; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing GSNOR Inhibitors

The GSNOR inhibitors of the invention can readily be synthesized using known synthetic methodologies or via a modification of known synthetic methodologies. As would be readily recognized by a skilled artisan, the methodologies described below allow the synthesis of pyrroles having a variety of substituents. Exemplary synthetic methods are described in the examples below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Method of Treatment

The invention encompasses methods of preventing or treating (e.g., alleviating one or more symptoms of) medical conditions through use of one or more of the disclosed compounds. The methods comprise administering a therapeutically effective amount of a GSNOR inhibitor to a patient in need. The compositions of the invention can also be used for prophylactic therapy.

The GSNOR inhibitor used in the methods of treatment according to the invention can be: (1) a novel GSNOR inhibitor described herein, or a pharmaceutically acceptable salt thereof, a prodrug thereof, or a metabolite thereof; (2) a compound which was known prior to the present invention, but wherein it was not known that the compound is a GSNOR inhibitor, or a pharmaceutically acceptable salt thereof, a prodrug thereof, or a metabolite thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

The disorders can include pulmonary disorders associated with hypoxemia and/or smooth muscle constriction in the lungs and/or lung infection and/or lung injury (e.g., pulmonary hypertension, ARDS, asthma, pneumonia, pulmonary fibrosis/interstitial lung diseases, cystic fibrosis COPD) cardiovascular disease and heart disease, including conditions such as hypertension, ischemic coronary syndromes, atherosclerosis, heart failure, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (ischemic or alcoholic)), impotence, obesity caused by eating in response to craving for food, stroke, reperfusion injury (e.g., traumatic muscle injury in heart or lung or crush injury), and disorders where preconditioning of heart or brain for NO protection against subsequent ischemic events is beneficial.

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine) and perfluorocarbons that have been saturated with NO or a hydrophobic NO donor.

The combination of a GSNOR inhibitor with R(+) enantiomer of amlodipine, a known NO releaser (Zhang X. P at al. 2002 J. Cardiovascular Pharmacology 39, 208-214) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including but not limited to pathologic bacteria, pathologic viruses, pathologic Chlamydia, pathologic protozoa, pathologic Rickettsia, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

In one embodiment, the treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, the treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof, can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, or metabolite thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefore include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-S-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Clans® (tadalafil), Levitra® (vardenifil), etc.), a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

In general, the dosage, i.e., the therapeutically effective amount, ranges from 1 μg to 10 g/kg and often ranges from 10 μg to 1 g/kg or 10 μg to 100 mg/kg body weight of the subject being treated, per day.

H. Other Uses

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a GSNOR inhibitor can be used to coat a surgical mesh or cardiovascular stent prior to implantation in a patient. The GSNOR inhibitors of the present invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to GSNOR inhibitor compounds, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-30 list representative novel pyrrole analogs of Formula I useful as GSNOR inhibitors of the invention. The synthetic methods that can be used to prepare each compound are detailed in Examples 1-30, with reference to synthetic schemes described in Example 31.

Example 1

3-(2-(4-carbamoyl-2-methylphenyl)-3-(4-methoxyphenyl)-1H-pyrrol-1-yl)propanoic acid

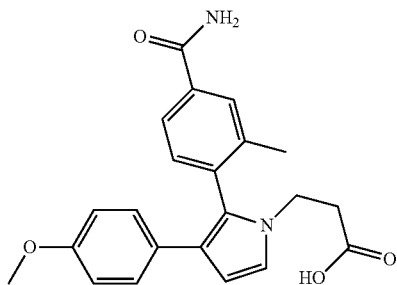 [SMILES: COc1ccc(-c2ccn(CCC(=O)O)c2-c2ccc(C(N)=O)cc2C)cc1]

Synthesis: Scheme 1, R=propanoic acid-3-yl with minor deviations. In step 1, the reaction was stirred at room temperature overnight and then purified by preparative TLC. In step 2, the mixture was stirred at room temperature overnight. Water was added and the mixture was washed with diethyl ether, the aqueous layer was adjusted to PH=4-5 with 1 N hydrochloric acid. The resulting mixture was extracted with ethyl acetate (30 mL×4). The combined organic layer was washed with brine, dried over sodium sulfate, and evaporated. The residue was purified on silica gel column (eluting with 5% methanol in dichloromethane), followed by preparative HPLC to give the title compound.

Characterization Data: $^1$H NMR (DMSO-$d_6$, 400 MHz TMS): δ 8.01 (brs, 1H), 7.79 (s, 1H), 7.77 (d, J=8.0 Hz, 1H), 7.39 (brs, 1H), 7.35 (d, J=8.0 Hz, 1H), 6.93 (m, 3H), 6.70 (d, J=8.8 Hz, 2H), 6.35 (d, J=2.8 Hz, 1H), 3.88 (m, 1H), 3.74 (m, 1H), 3.63 (s, 3H), 2.42 (t, J=7.2 Hz, 2H), 1.91 (s, 3H); MS (ESI): m/z 379.1 [M+1]$^+$.

Example 2

3-(2-(4-carbamoyl-2-methylphenyl)-3-(4-methoxyphenyl)-1H-pyrrol-1-yl)-3-phenylpropanoic acid

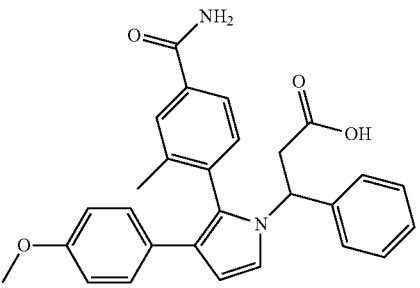 [SMILES: COc1ccc(-c2ccn(C(CC(=O)O)c3ccccc3)c2-c2ccc(C(N)=O)cc2C)cc1]

Synthesis: Scheme 1, R=3-phenylpropanoic acid-3-yl

Characterization Data: $^1$H NMR (CD$_3$OD 400 MHz TMS): δ 7.76 (d, J=8.0 Hz, 0.5 H), 7.68 (s, 0.4 H), 7.54 (d, J=8.0 Hz, 0.6H), 7.43 (s, 0.5H), 7.35 (d, J=8.0 Hz, 0.5H), 7.19-7.13 (m, 2H), 7.08-7.04 (m, 2H), 6.88-6.85 (m, 3H), 6.74-6.71 (m, 1H), 6.61 (d, J=8 Hz, 0.4H), 6.55 (d, J=8.8 Hz, 2H), 6.41 (d, J=2.8 Hz, 0.4H), 6.36 (d, J=2.8 Hz, 0.5H), 5.42-5.38 (m, 0.6H), 5.14-5.10 (m, 0.4H), 3.58 (s, 3H), 3.28-3.24 (m, 0.5H), 3.11-3.03 (m, 0.5H), 3.00-2.93 (m, 1H), 1.99 (s, 1.3H), 1.21 (s, 1.7H); MS (ESI): m/z 477.1 [M+23]$^+$.

Example 3

3-(2-(4-carbamoyl-2-methylphenyl)-3-(4-methoxyphenyl)-1H-pyrrol-1-yl)-2-methylpropanoic acid

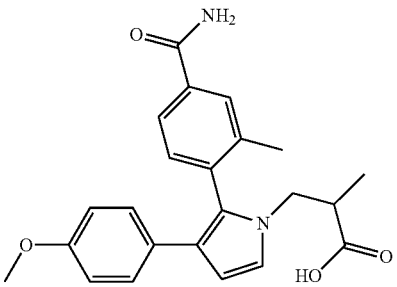 [SMILES: COc1ccc(-c2ccn(CC(C)C(=O)O)c2-c2ccc(C(N)=O)cc2C)cc1]

Synthesis: Scheme 1, R=Scheme 1, R=2-methylpropanoic acid-3-yl

Characterization Data: $^1$H NMR (CD$_3$OD 400 MHz TMS): δ 7.80 (d, J=7.2 Hz, 2H), 7.40 (d, J=7.6 Hz, 1H), 6.98 (d, J=8.8 Hz, 2H), 6.88 (dd, J$_1$=1.6 Hz, J$_2$=5.6 Hz, 1H), 6.69 (d, J=8.4 Hz, 2H), 6.37 (dd, J$_1$=2.8 Hz, J$_2$=7.2 Hz, 0.6H), 4.19-4.13 (m, 0.6H), 3.99-3.93 (m, 0.4H), 3.86-3.81 (m, 0.5H), 3.72 (s, 3H), 3.62-3.57 (m, 0.6H), 2.57-2.49 (m, 1H), 2.04 (s, 3H), 0.95 (dd, J=2.8 Hz, J=7.2 Hz, 3H); MS (ESI): m/z 393.0 [M+1]+.

Example 4

4-(2-(4-carbamoyl-2-methylphenyl)-3-(4-methoxyphenyl)-1H-pyrrol-1-yl)butanoic acid

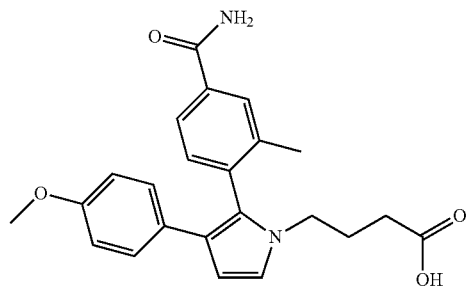 [SMILES: COc1ccc(-c2ccn(CCCC(=O)O)c2-c2ccc(C(N)=O)cc2C)cc1]

Synthesis: Scheme 1, R=n-butanoic acid-4-yl

Characterization Data: ¹H NMR (G000003136 00125-061-1 CD₃OD 400 MHz TMS): δ 7.79 (s, 1H), 7.78 (d, J=7.6 Hz, 1H), 7.37 (d, J=8.0 Hz, 1H), 6.99 (d, J=8.8 Hz, 2H), 6.88 (d, J=2.8 Hz, 1H), 6.69 (d, J=8.8 Hz, 2H), 6.40 (d, J=2.8 Hz, 1H), 3.90-3.84 (m, 1H), 3.66 (s, 3H), 3.39-3.63 (m, 1H), 2.13 (m, 2H), 2.03 (m, 3H), 1.78-1.70 (m, 2H); MS (ESI): m/z 394.1 [M+1]+.

Example 5

3-(3-(4-(1H-imidazol-1-yl)phenyl)-2-(4-carbamoyl-2-methylphenyl)-1H-pyrrol-1-yl)propanoic acid

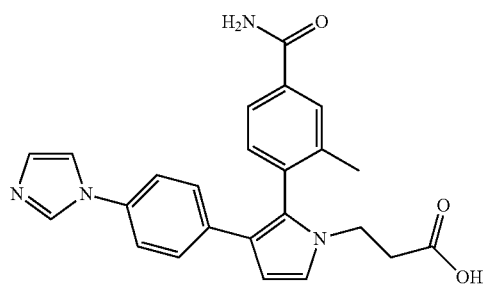 [SMILES: Cc1cc(C(N)=O)ccc1-c1c(-c2ccc(-n3ccnc3)cc2)ccn1CCC(=O)O]

Synthesis: Scheme 2, R1=propanoic acid-3-yl, R2=1H-imidazol-1-yl

Characterization Data: ¹H NMR (DMSO-d₆, 400 MHz): δ 9.33 (s, 1 H), 8.11-8.06 (m, 2 H), 7.87 (s, 1 H), 7.83 (d, J=8.4 Hz, 1 H), 7.73 (s, 1 H), 7.56-7.54 (d, J=8.4 Hz, 2 H), 7.44 (m, 3 H), 7.21 (d, J=8.4 Hz, 2 H), 7.05 (d, J=2.8 Hz, 1 H), 6.57 (d, J=3.2 Hz, 1 H), 3.93-3.88 (m, 2 H), 3.79-3.74 (m, 2 H), 2.09 (s, 3 H); MS (ESI): m/z 415.3 [M+1]+.

Example 6

3-(2-(4-carbamoyl-2-methylphenyl)-1-(4-methoxyphenyl)-1H-pyrrol-3-yl)propanoic acid

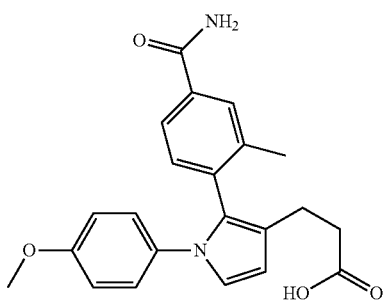 [SMILES: COc1ccc(-n2ccc(CCC(=O)O)c2-c2ccc(C(N)=O)cc2C)cc1]

Synthesis: Scheme 4, R1=4-methoxyphenyl

Characterization Data: ¹H NMR (CDCl₃ 400 MHz TMS): δ 7.48 (d, J=8.2 Hz, 1H), 7.47 (s, 1H), 7.23 (d, J=7.2 Hz, 2H), 6.80 (m, 3H), 6.63 (d, J=8.8 Hz, 2H), 3.66 (s, 3H), 2.57 (m, 2H), 2.45 (m, 2H), 1.85 (s, 3H); MS (ESI): m/z 379.2 [M+1]+.

Example 7

3-(2-(4-carbamoyl-2-methylphenyl)-3-(4-methoxyphenyl)-1H-pyrrol-1-yl)butanoic acid

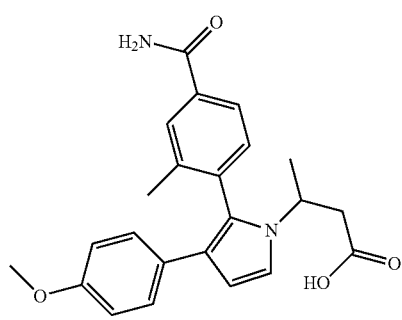 [SMILES: COc1ccc(-c2ccn(C(C)CC(=O)O)c2-c2ccc(C(N)=O)cc2C)cc1]

Synthesis: Scheme 1, R=butanoic acid-3-yl

Characterization Data: ¹H NMR (CD₃OD 400 MHz TMS): δ 7.79-7.7 (m, 2H), 7.48 (d, J=8.4 Hz, 1H), 6.99-6.96 (m, 3H), 6.67 (d, J=8.8 Hz, 2H), 6.42 (d, J=3.2 Hz, 1H), 4.29-4.24 (m, 1H), 3.70 (s, 3H), 2.87-2.81 (m, 1H), 2.74-2.67 (m, 1H), 2.00 (s, 3H), 1.30 (d, J=6.8 Hz, 3H); MS (ESI): m/z 393.1 [M+1]+.

Example 8

1-((2-(4-carbamoyl-2-methylphenyl)-3-(4-methoxyphenyl)-1H-pyrrol-1-yl)methyl)cyclopropanecarboxylic acid

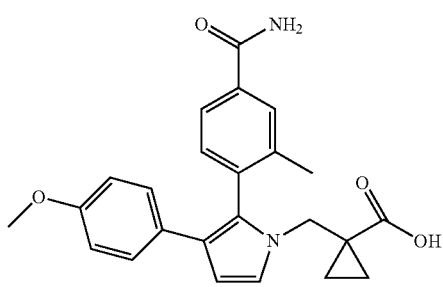 [SMILES: COc1ccc(-c2ccn(CC3(C(=O)O)CC3)c2-c2ccc(C(N)=O)cc2C)cc1]

Synthesis: Scheme 1, R=1-methyl cyclopropanecarboxylic acid

Characterization Data: ¹H NMR (CD₃OD 300 MHz TMS): δ 7.76 (m, 2H), 7.36 (d, J=7.8 Hz, 1H), 7.05 (d, J=3.0 Hz, 1H), 6.97 (d, J=9.0 Hz, 2H), 6.68 (d, J=9.0 Hz, 2H), 6.36 (d, J=3.0

Hz, 1H), 3.95 (s, 2H), 3.71 (s, 3H), 2.01 (s, 3H), 1.19 (m, 2H), 0.76-0.72 (m, 1H), 0.59-0.55 (m, 1H); MS (ESI): m/z 427.1 [M+23]⁺.

Example 9

3-(2-(4-carbamoyl-2-methylphenyl)-3-(4-methoxyphenyl)-1H-pyrrol-1-yl)-2,2-difluoropropanoic acid

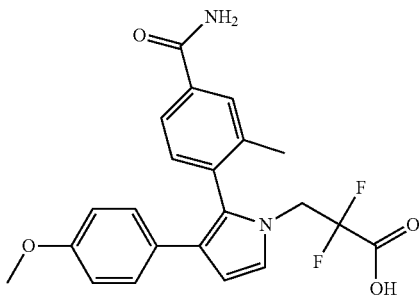 [SMILES: COc1ccc(-c2ccn(CC(F)(F)C(=O)O)c2-c2ccc(C(N)=O)cc2C)cc1]

Synthesis: Scheme 1, R=2,2-difluoropropanoic acid-3-yl

Characterization Data: $^1$H NMR (CD$_3$OD 400 MHz TMS): δ 7.80-7.78 (m, 2H), 7.38 (d, J=7.6 Hz, 1H), 7.00-6.95 (m, 3H), 6.71-6.69 (m, 2H), 6.45 (d, J=2.8 Hz, 1H), 4.50-4.39 (m, 1H), 4.31-4.20 (m, 1H), 3.72 (s, 3H), 1.97 (s, 3H); MS (ESI): m/z 414.1 [M+1]⁺.

Example 10

3-(2-(4-carbamoyl-2-methylphenyl)-3-(4-methoxyphenyl)-1H-pyrrol-1-yl)-2-hydroxypropanoic acid

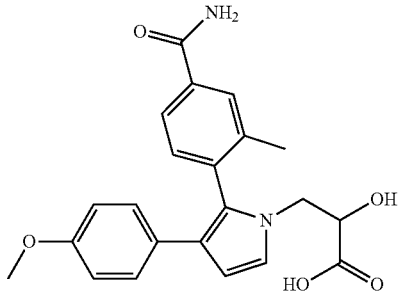 [SMILES: COc1ccc(-c2ccn(CC(O)C(=O)O)c2-c2ccc(C(N)=O)cc2C)cc1]

Synthesis: Scheme 1, R=2-hydroxypropanoic acid-3-yl

Characterization Data: $^1$H NMR (CD$_3$OD 400 MHz TMS): δ 7.78-7.76 (m, 2H), 7.44-7.39 (m, 1H), 6.99-6.96 (m, 3H), 6.67 (d, J=8.4 Hz, 2H), 6.37 (d, J=3.2 Hz, 1H), 4.20-4.12 (m, 1H), 4.07-4.04 (m, 0.5H), 4.00-3.89 (m, 1H), 3.81-3.75 (m, 0.5H), 3.70 (s, 3H), 2.01 (m, 3H); MS (ESI): m/z 395.1 [M+1]⁺.

Example 11

3-(2-(4-carbamoyl-2-methylphenyl)-3-(4-methoxyphenyl)-1H-pyrrol-1-yl)hexanoic acid

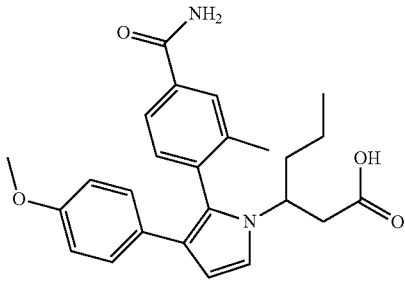 [SMILES: CCCC(CC(=O)O)n1ccc(-c2ccc(OC)cc2)c1-c1ccc(C(N)=O)cc1C]

Synthesis: Scheme 1, R=hexanoic acid-3-yl

Characterization Data: $^1$H NMR (CD$_3$OD 300 MHz TMS): δ 7.82 (dd, J=1.5 Hz, J=8.1 Hz, 1H), 7.74 (s, 1H), 7.56 (d, J=7.8 Hz, 1H), 6.99-6.96 (m, 3H), 6.68 (d, J=8.7 Hz, 2H), 6.43 (d, J=3.0 Hz, 1H), 4.27-4.17 (m, 1H), 3.71 (s, 3H), 2.94-2.75 (m, 2H), 1.92 (s, 3H), 1.76-1.56 (m, 2H), 1.14-0.92 (m, 2H), 0.70 (t, J=7.2 Hz, 3H); MS (ESI): m/z=421.2 [M+1]⁺.

Example 12

3-(2-(4-carbamoyl-2-methylphenyl)-3-(4-methoxyphenyl)-1H-pyrrol-1-yl)-4-methylpentanoic acid

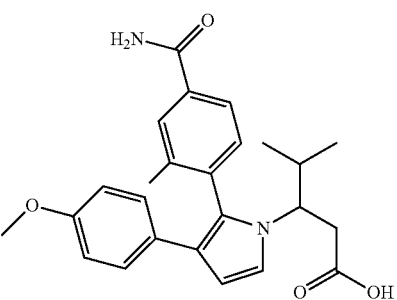 [SMILES: COc1ccc(-c2ccn(C(CC(=O)O)C(C)C)c2-c2ccc(C(N)=O)cc2C)cc1]

Synthesis: Scheme 1, R=4-methylpentanoic acid-3-yl, with a deviation in step 1. 2 equivalents of HOAc was used in place of PPTS and the reaction was stirred at 120° C. under microwave irradiation for 1 hour. Mixture was concentrated in vacuo to afford the crude compound, which was used directly in the next step.

Characterization Data: $^1$H NMR (CD$_3$OD 400 MHz TMS): δ 7.81 (d, J=7.6 Hz, 1H), 7.70-7.67 (m, 2H), 6.96-6.94 (m, 3H), 6.68 (d, J=8.8 Hz, 2H), 6.39 (d, J=2.8 Hz, 1H), 4.18-4.12

(m, 1H), 3.71 (s, 3H), 2.93-2.89 (m, 2H), 1.89-1.85 (m, 4H), 0.79 (d, J=6.8 Hz, 3H), 0.60 (d, J=6.8 Hz, 3H); MS (ESI): m/z 443.1 [M+23]⁺.

7.29 (s,1H), 7.00-7.15 (m, 3H), 6.80-6.95 (m, 2H), 6.21 (s, 1H), 3.60 (s, 3H), 2.37-2.42 (m, 4H), 2.00 (s, 3H); MS (ESI): m/z 413.0 [M+1]⁺.

Example 13

3-(1-(4-(1H-imidazol-1-yl)phenyl)-2-(4-carbamoyl-2-methylphenyl)-1H-pyrrol-3-yl)propanoic acid

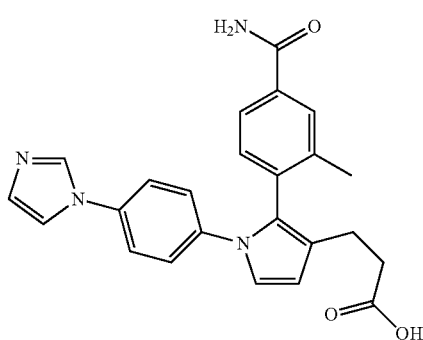 [SMILES: Cc1cc(C(N)=O)ccc1-c1c(CCC(=O)O)ccn1-c1ccc(-n2ccnc2)cc1]

Synthesis: Scheme 5, R1=(1H-imidazol-1-yl)phenyl.

Characterization Data: ¹H NMR (CD₃OD, 400 MHz TMS): δ 8.14 (brs, 1H), 7.74 (d, J=8.0 Hz, 1H), 7.68 (s, 1H), 7.55 (brs, 1H), 7.49 (d, J=8.4 Hz, 2H), 7.42 (d, J=8.0 Hz, 1H), 7.24 (d, J=8.4 Hz, 2H), 7.15 (s, 1H), 7.08 (d, J=2.0 Hz, 1H), 6.37 (d, J=2.8 Hz, 1H), 2.64 (m, 2H), 2.49 (m, 2H), 1.97 (s, 3H); MS (ESI): m/z 415.2 [M+1]⁺.

Example 14

3-(2-(4-carbamoyl-2-methylphenyl)-1-(4-chloro-2-methoxyphenyl)-1H-pyrrol-3-yl)propanoic acid

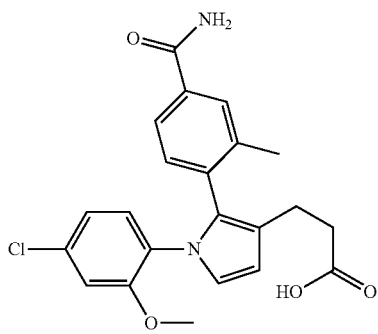 [SMILES: COc1cc(Cl)ccc1-n1ccc(CCC(=O)O)c1-c1ccc(C(N)=O)cc1C]

Synthesis: Scheme 3, R1=4-chloro-2-methoxyphenyl

Characterization Data: ¹H NMR (DMSO-d₆ 400 MHz TMS): δ 7.87 (s, 1H), 7.64 (s, 1H), 7.55 (d, J=7.6 Hz,1H),

Example 15

4-(2-(4-carbamoyl-2-methylphenyl)-3-(4-methoxyphenyl)-1H-pyrrol-1-yl)-2-hydroxybenzoic acid

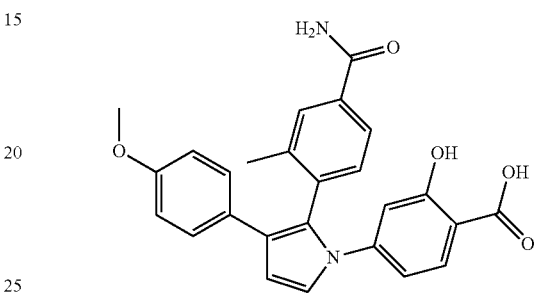

Synthesis: Scheme 1, R=4-carboxy-3-hydroxyphenyl

Characterization Data: ¹H NMR (CD₃OD 400 MHz TMS): δ 7.62-7.58 (m, 2H), 7.52 (d, J=7.6 Hz, 1H), 7.11-7.06 (m, 2H), 6.92 (d, J=8.8 Hz, 2H), 6.63 (d, J=8.8 Hz, 2H), 6.50-6.47 (m, 3H), 3.62 (s, 3H), 1.85 (s, 3H); MS (ESI): m/z 443.0 [M+1]⁺.

Example 16

4-(2-(4-carbamoyl-2-methylphenyl)-3-(4-methoxyphenyl)-1H-pyrrol-1-yl)-2-fluorobenzoic acid

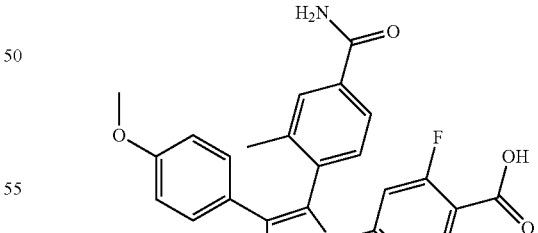

Synthesis: Scheme 1, R=4-carboxy-3-fluoro phenyl

Characterization Data: ¹H NMR (CD₃OD 400 MHz TMS): δ 7.84 (t, J=8 Hz, 1H), 7.73 (s, 1H), 7.67 (d, J=7.6 Hz, 1H), 7.26-7.24 (m, 2H), 7.06 (d, J=8.8 Hz, 2H), 6.99-6.91 (m, 2H), 6.77 (d, J=8.4 Hz, 2H), 6.65 (d, J=3.2 Hz, 1H), 3.76 (s, 3H), 1.98 (s, 3H); MS (ESI): m/z 445.0 [M+1]+.

Example 17

4-(1-(4-hydroxy-3-nitrophenyl)-3-(4-methoxyphenyl)-1H-pyrrol-2-yl)-3-methylbenzamide

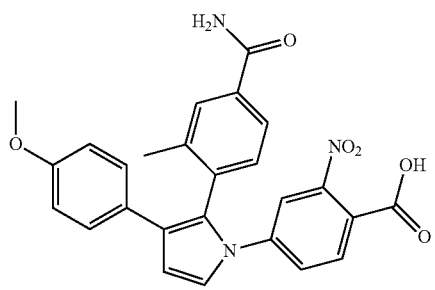 [SMILES: COc1ccc(-c2ccn(-c3ccc(C(=O)O)c([N+](=O)[O-])c3)c2-c2ccc(C(N)=O)cc2C)cc1]

Synthesis: Scheme 1, R=4-hydroxy-3-nitrophenyl

Characterization Data: $^1$H NMR (CD$_3$OD 400 MHz TMS): δ 7.78 (t, J=2.4 Hz, 1H), 7.69 (s, 1H), 7.64 (d, J=8.0 Hz, 1H), 7.4 (dd, J=2.8 Hz, J=8.8 Hz, 1H), 7.24 (d, J=7.6 Hz, 1H), 7.13 (d, J=2.8 Hz, 1H), 7.07-7.03 (m, 3H), 6.74 (d, J=8.4 Hz, 2H), 6.60 (d, J=3.2 Hz, 1H), 3.74 (s, 3H), 1.98 (s, 3H); MS (ESI): m/z 444.0 [M+1]+.

Example 18

4-(1-(6-hydroxypyridin-3-yl)-3-(4-methoxyphenyl)-1H-pyrrol-2-yl)-3-methylbenzamide

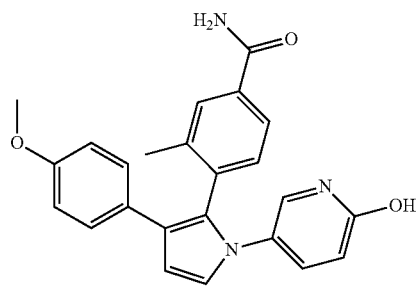 [SMILES: COc1ccc(-c2ccn(-c3ccc(O)nc3)c2-c2ccc(C(N)=O)cc2C)cc1]

Synthesis: Scheme 1, R=6-hydroxypyridin-3-yl

Characterization Data: $^1$H NMR (CD$_3$OD 400 MHz TMS): δ 7.72 (s, 1H), 7.68 (d, J=7.6 Hz, 1H), 7.43 (dd, J=2.8 Hz, J=8.8 Hz, 1H), 7.35 (d, J=2.8 Hz, 1H), 7.28 (d, J=8.0 Hz, 1H), 7.07-7.05 (m, 3H), 6.74 (d, J=8.8 Hz, 2H), 6.59 (d, J=2.8 Hz, 1H), 6.46 (d, J=8.4 Hz, 1H), 3.74 (s, 3H), 2.00 (s, 3H); MS (ESI): m/z 400.0 [M+1]+.

Example 19

4-(2-(4-carbamoyl-2-methylphenyl)-3-(4-methoxyphenyl)-1H-pyrrol-1-yl)benzoic acid

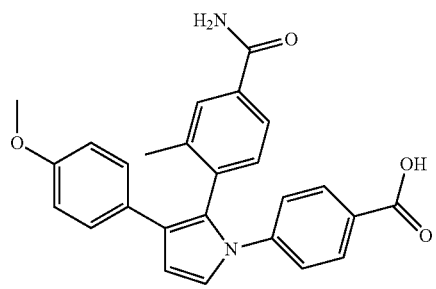 [SMILES: COc1ccc(-c2ccn(-c3ccc(C(=O)O)cc3)c2-c2ccc(C(N)=O)cc2C)cc1]

Synthesis: Scheme 1, R=4-carboxyphenyl

Characterization Data: $^1$H NMR (DMSO-d$_6$ 400 MHz TMS): δ 7.95 (s, 1H), 7.83 (d, J=8.8 Hz, 2H), 7.67 (s, 1H), 7.63 (m, 1H), 7.37 (s, 1H), 7.29 (d, J=2.8 Hz, 1H), 7.22 (d, J=7.6 Hz, 1H), 7.16 (d, J=8.8 Hz, 2H), 7.02 (d, J=8.8 Hz, 2H), 6.77 (d, J=8.8 Hz, 2H), 6.63 (d, J=2.8 Hz, 1H), 3.68 (s, 3H), 1.85 (s, 3H); MS (ESI): m/z 427.2 [M+1]+.

Example 20

4-(2-(4-carbamoyl-2-methylphenyl)-3-(4-methoxyphenyl)-1H-pyrrol-1-yl)-2-chlorobenzoic acid

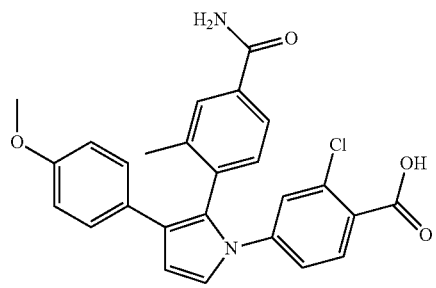 [SMILES: COc1ccc(-c2ccn(-c3ccc(C(=O)O)c(Cl)c3)c2-c2ccc(C(N)=O)cc2C)cc1]

Synthesis: Scheme 1, R=3-chloro-4-carboxyphenyl

Characterization Data: $^1$H NMR (DMSO-d$_6$ 400 MHz TMS): δ 13.42 (brs, 1H), 7.97 (s, 1H), 7.71-7.66 (m, 3H), 7.36

(m, 2H), 7.26 (d, J=7.6 Hz, 2H), 7.03 (m, 3H), 6.78 (d, J=8.4 Hz, 2H), 6.65 (d, J=2.8 Hz, 1H), 3.68 (s, 3H), 1.86 (s, 3H); MS (ESI): m/z 483.2 [M+23]⁺.

Example 21

4-(3-(4-methoxyphenyl)-1-(2-(trifluoromethylsulfonamido)ethyl)-1H-pyrrol-2-yl)-3-methylbenzamide

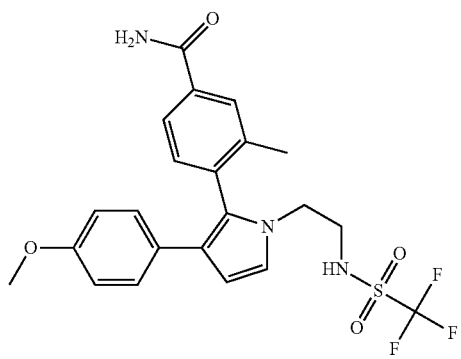 [SMILES: COc1ccc(-c2ccn(CCNS(=O)(=O)C(F)(F)F)c2-c2ccc(C(N)=O)cc2C)cc1]

Synthesis: Scheme 6

Characterization Data: ¹H NMR (CD$_3$OD 400 MHz TMS): δ 7.84-7.79 (m, 2H), 7.41 (d, J=7.6 Hz, 1H), 7.00 (d, J=8.8 Hz, 2H), 6.92 (d, J=2.8 Hz, 1H), 6.70 (d, J=8.8 Hz, 2H), 6.44 (d, J=2.8 Hz, 1H), 3.98-3.92 (m, 1H), 3.81-3.72 (m, 4H), 3.24 (t, J=6.4 Hz, 2H), 2.03 (s, 3H); MS (ESI): m/z 482.1 [M+1]⁺.

Example 22

4-(3-(4-methoxyphenyl)-1-(4-sulfamoylphenyl)-1H-pyrrol-2-yl)-3-methylbenzamide

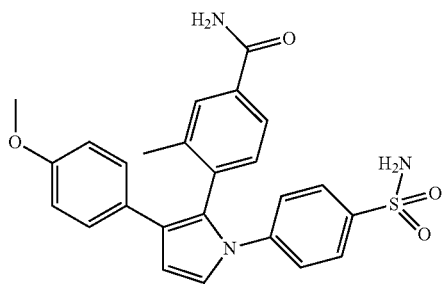 [SMILES: COc1ccc(-c2ccn(-c3ccc(S(N)(=O)=O)cc3)c2-c2ccc(C(N)=O)cc2C)cc1]

Synthesis: Scheme 1, R=4-sulfamoylphenyl

Characterization Data: ¹H NMR (CD$_3$OD 400 MHz TMS): δ 7.78 (d, J=8.8 Hz, 2H), 7.67 (s, 1H), 7.61 (d, J=8.0 Hz, 1H), 7.23-7.19 (m, 4H), 7.04 (d, J=8.8 Hz, 2H), 6.74 (d, J=8.8 Hz, 2H), 6.62 (d, J=4.4 Hz, 1H), 3.05 (s, 3H), 1.94 (s, 3H); MS (ESI) m/z: [M+23]⁺=484.0.

Example 23

4-(1-(3-fluoro-4-hydroxyphenyl)-3-(4-methoxyphenyl)-1H-pyrrol-2-yl)-3-methylbenzamide

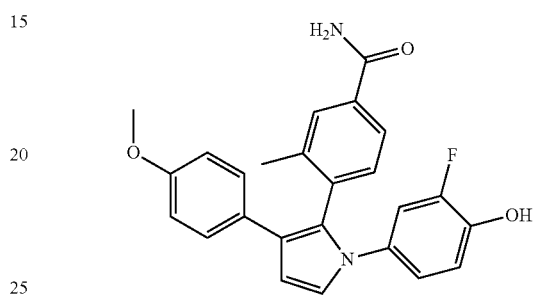

Synthesis: Scheme 1, R=3-fluoro-4-hydroxyphenyl, Step 1 uses 4-amino-2-fluorophenol (2A-1) described in Scheme 2A Characterization Data: ¹H NMR (CD$_3$OD 400 MHz TMS): δ 7.67 (s, 1H), 7.61 (d, J=8.0 Hz, 1H), 7.20 (d, J=7.6 Hz, 1H), 7.04-7.02 (m, 3H), 6.82-6.71 (m, 5H), 6.53 (d, J=2.8 Hz, 1H), 3.73 (s, 3H), 1.96 (s, 3H); MS (ESI) m/z: [M+1]⁺=417.1.

Example 24

5-(2-(4-carbamoyl-2-methylphenyl)-3-(4-methoxyphenyl)-1H-pyrrol-1-yl)picolinic acid

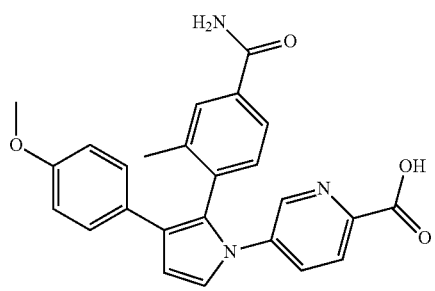 [SMILES: COc1ccc(-c2ccn(-c3ccc(C(=O)O)nc3)c2-c2ccc(C(N)=O)cc2C)cc1]

Synthesis: Scheme 1, R=6-carboxypyridin-3-yl

Characterization Data: ¹H NMR (CD$_3$OD 400 MHz TMS): δ 8.36 (s, 1H), 8.09 (d, J=8.4 Hz, 1H), 7.72-7.70 (m, 2H), 7.66 (d, J=8.0 Hz, 1H), 7.30 (d, J=2.8 Hz, 1H), 7.24 (d, J=8.0 Hz, 1H), 7.07 (d, J=8.8 Hz, 2H), 6.77 (d, J=8.8 Hz, 2H), 6.71 (d, J=2.8 Hz, 1H), 3.75 (s, 3H), 1.97 (s, 3H); MS (ESI) m/z: [M+1]⁺=428.2.

Example 25

4-(1-(3,5-difluoro-4-hydroxyphenyl)-3-(4-methoxyphenyl)-1H-pyrrol-2-yl)-3-methylbenzamide

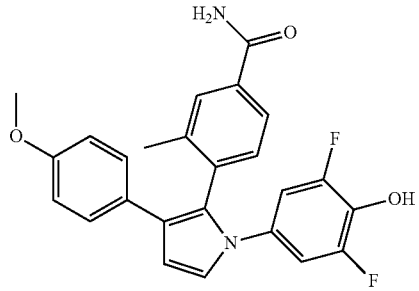 [SMILES: COc1ccc(-c2ccn(-c3cc(F)c(O)c(F)c3)c2-c2ccc(C(N)=O)cc2C)cc1]

Synthesis: Scheme 1, R=3,5-difluoro-4-hydroxyphenyl

Characterization Data: ¹H NMR (CDCl₃ 400 MHz TMS): δ 7.59 (s, 1H), 7.47-7.49 (d, J=6.8 Hz,1H), 7.14-7.16 (d, J=8.0 Hz,1H), 6.97-6.99 (d, J=8.8 Hz, 2H), 6.90-6.91(d, 1H), 6.68-6.71 (d, J=8.8 Hz, 2H), 6.56-6.58 (d, J=7.6 Hz, 2H), 6.51-6.52 (d, 1H), 3.72 (s, 3H), 1.91 (s, 3H); MS (ESI): m/z 435.0 [M+1]⁺.

Example 26

4-(1-(5-hydroxypyridin-2-yl)-3-(4-methoxyphenyl)-1H-pyrrol-2-yl)-3-methylbenzamide

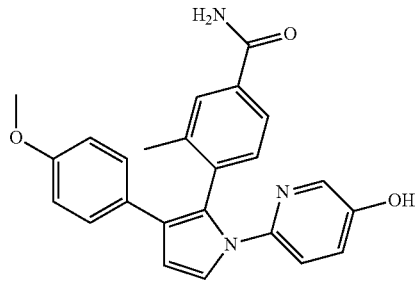 [SMILES: COc1ccc(-c2ccn(-c3ccc(O)cn3)c2-c2ccc(C(N)=O)cc2C)cc1]

Synthesis: Scheme 1, R=5-hydroxypyridin-2-yl, with modification of Step 1, where 1 equivalent of AcOH was used instead of PPTS, and the reaction was heated at 80° C. for 3 days. Purification by prep TLC.

Characterization Data: ¹H NMR (CD₃OD 400 MHz TMS): δ 7.80 (d, J=3.2 Hz, 1H), 7.56 (s, 1H), 7.50 (d, J=8.0 Hz, 1H), 7.14 (d, J=2.8 Hz, 1H), 7.08 (d, J=8.0 Hz, 1H), 6.94-6.89 (m, 3H), 6.62 (d, J=8.8 Hz, 2H), 6.52 (d, J=8.8 Hz, 2H), 6.44 (d, J=2.8 Hz, 1H), 3.62 (s, 3H), 1.84 (s, 3H); MS (ESI) m/z: [M+1]⁺=400.1.

Example 27

5-(2-(4-carbamoyl-2-methylphenyl)-3-(4-methoxyphenyl)-1H-pyrrol-1-yl)-2-hydroxybenzoic acid

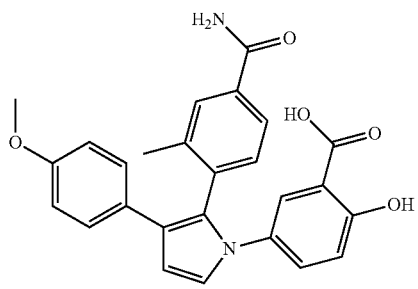 [SMILES: COc1ccc(-c2ccn(-c3ccc(O)c(C(=O)O)c3)c2-c2ccc(C(N)=O)cc2C)cc1]

Synthesis: Scheme 1, R=2-hydroxybenzoic acid-4-yl, with modification of Step 1, where 1 equivalent of AcOH was used instead of PPTS.

Characterization Data: ¹H NMR (DMSO-d₆ 400 MHz TMS): δ 7.92 (br, 1H), 7.64 (s, 1H), 7.60 (d, J=8.0 Hz, 1H), 7.46 (d, J=2.4 Hz, 1H), 7.33 (br, 1H), 7.20-7.17 (m, 2H), 7.13 (d, J=3.2 Hz, 1H), 6.98 (d, J=8.8 Hz, 2H), 6.83 (d, J=8.8 Hz, 1H), 6.74 (d, J=8.4 Hz, 2H), 6.54 (d, J=2.8 Hz, 1H), 3.65 (s, 3H), 1.85 (s, 3H); MS (ESI) m/z: [M+1]⁺=443.1.

Example 28

6-(2-(4-carbamoyl-2-methylphenyl)-3-(4-methoxyphenyl)-1H-pyrrol-1-yl)nicotinic acid

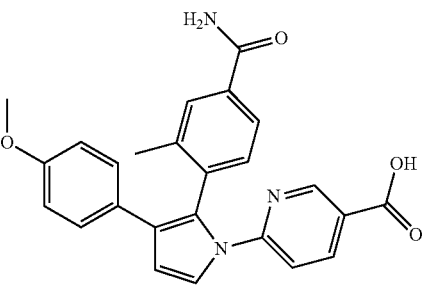 [SMILES: COc1ccc(-c2ccn(-c3ccc(C(=O)O)cn3)c2-c2ccc(C(N)=O)cc2C)cc1]

Synthesis: Scheme 1, R=5-carboxypyridin-2-yl, with modification of Step 1, where AcOH was used as solvent instead of EtOH. The reaction was heated at 130° C. for 4 hours. The mixture was concentrated in vacuo, and the crude product was purified by reverse-phase preparatory HPLC (26-53% acetonitrile+0.1% trifluoroacetic acid in water+0.1% trifluoroacetic acid, over 15 min.).

Characterization Data: ¹H NMR (DMSO-d₆ 400 MHz TMS): δ 8.78 (s, 1H), 7.98 (s, 1H), 7.72 (s, 1H), 7.66 (d, J=8.0, 1H), 7.56 (s, 1H), 7.37 (s, 1H), 7.21 (d, J=7.6, 1H), 7.03 (d, J=8.4, 2H), 6.78 (d, J=8.8, 2H), 6.70 (d, J=6.8, 1H), 6.63 (d, J=2.8, 1H), 3.69 (s, 3H), 1.86 (s, 1H); MS (ESI): m/z 428.2 [M+1]+.

Example 29

4-(1-(3-fluoro-4-hydroxyphenyl)-3-(4-(2-methyl-1H-imidazol-1-yl)phenyl)-1H-pyrrol-2-yl)-3-methylbenzamide

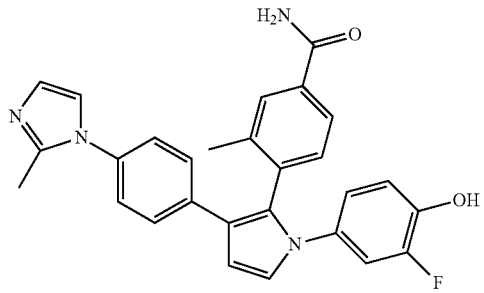 [SMILES: Cc1cc(C(N)=O)ccc1-c1c(-c2ccc(-n3ccnc3C)cc2)ccn1-c1ccc(O)c(F)c1]

Synthesis: Scheme 2A
Characterization Data: ¹H NMR (CD₃OD, 400 MHz, TMS): δ 7.63 (s, 1H), 7.59 (d, J=8.4 Hz, 1H), 7.55 (d, J=2.0 Hz, 1H), 7.50 (d, J=2.0 Hz, 1H), 7.33-7.27 (m, 4H), 7.22 (d, J=8.0 Hz, 1H), 7.04 (d, J=2.8 Hz, 1H), 6.88 (d, J=12.0 Hz, 1H), 6.75-6.68 (m, 2H), 6.64 (d, J=2.8 Hz, 1H), 2.48 (s, 3H), 1.93 (s, 3H); MS (ESI): m/z 467.2 [M+1]+.

Example 30

4-(1-(3,5-difluoro-4-hydroxyphenyl)-3-(4-(2-methyl-1H-imidazol-1-yl)phenyl)-1H-pyrrol-2-yl)-3-methyl-benzamide

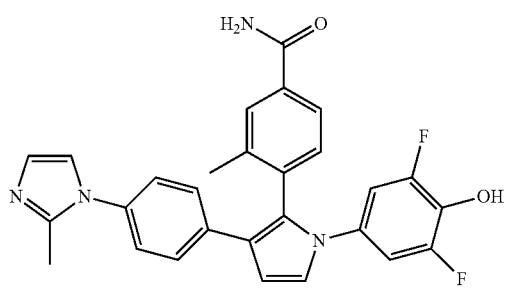 [SMILES: Cc1cc(C(N)=O)ccc1-c1c(-c2ccc(-n3ccnc3C)cc2)ccn1-c1cc(F)c(O)c(F)c1]

Synthesis: Scheme 2, R1=3,5-difluoro-4-hydroxyphenyl, R2=2-methyl-1H-imidazol-1-yl
Characterization Data: ¹H NMR (CD₃OD, 400 MHz, TMS): δ 7.75 (s, 1H), 7.71 (d, J=8.0 Hz, 1H), 7.62 (d, J=2.0 Hz, 1H), 7.56 (d, J=2.0 Hz, 1H), 7.42-7.36 (m, 4H), 7.33 (d, J=8.0 Hz, 1H), 7.16 (d, J=3.2 Hz, 1H), 6.77-6.74 (m, 3H), 2.56 (s, 3H), 2.02 (s, 3H); MS (ESI): m/z 485.3 [M+1]+.

Example 31

General and Specific Methods of Preparing Novel GSNOR Pyrrole Inhibitors

This example describes schemes for preparing the GSNOR inhibitors depicted in Examples 1-30. The synthesis of 4 common intermediates, Intermediates A-D, are first described followed by the synthetic schemes. Some schemes are specific to a particular compound, while others are general schemes that include an exemplary method for preparing a representative compound.

Synthesis of Common Intermediate A, 4-(2-(4-methoxyphenyl)-4-oxobutanoyl)-3-methylbenzonitrile

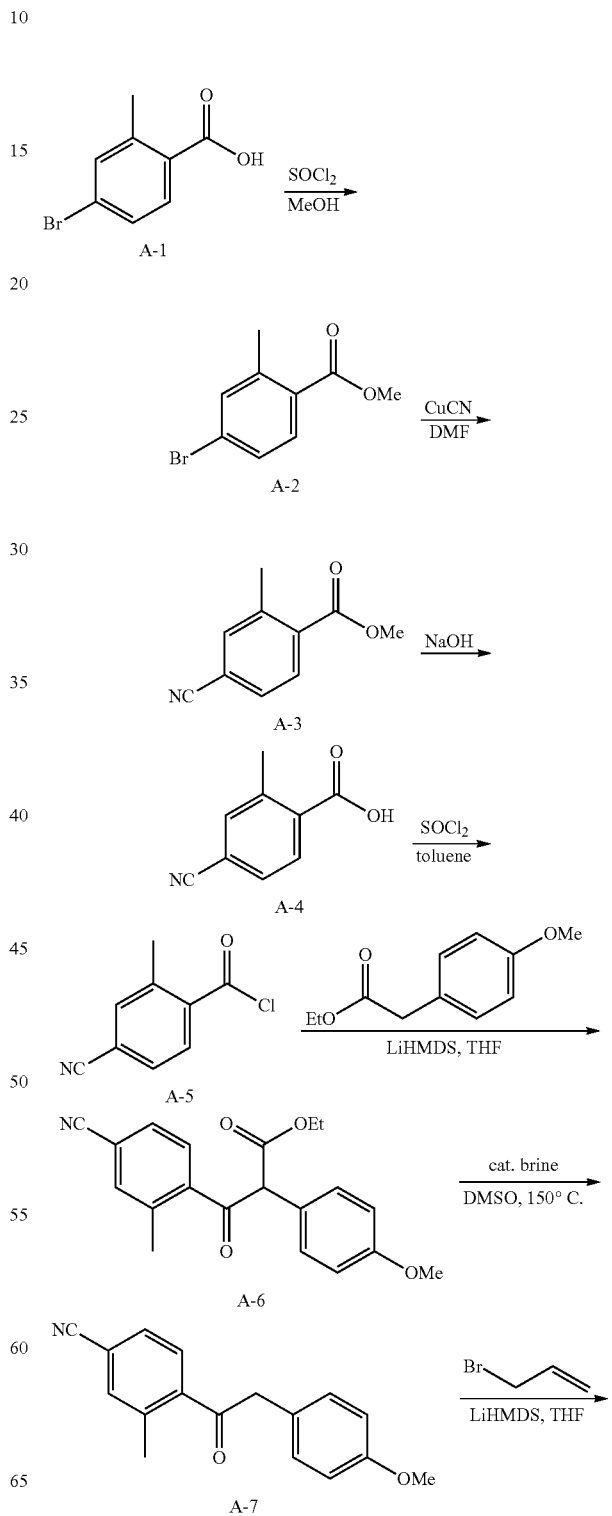

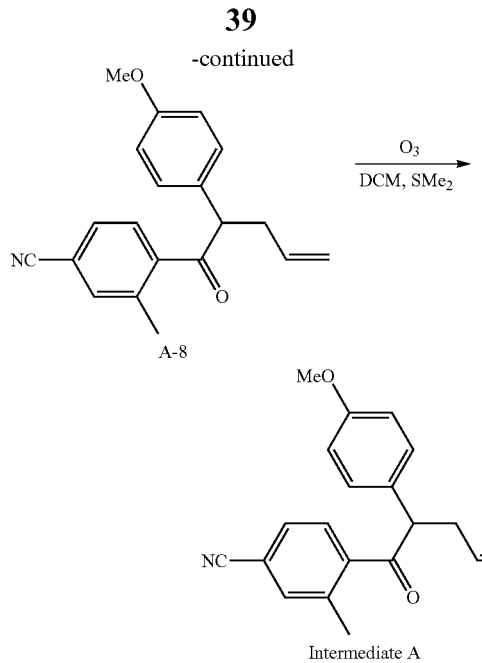

Synthesis of A-2, (methyl 4-bromo-2-methylbenzoate). To a solution of compound 1 (79.45 g, 369.5 mmol) in methanol (450 mL) was added thionyl chloride (53.6 mL, 739 mmol), and the mixture was stirred at 70° C. for 6 h. The reaction mixture was concentrated to afford A-2 (86.37 g, yield 100%). $^1$H NMR (CDCl$_3$ 300 MHz, TMS): δ 7.77 (d, J=8.4 Hz, 1H), 7.40-7.34 (m, 2H), 3.87 (s, 3H), 2.56 (s, 3H).

Synthesis of A-3, (methyl 4-cyano-2-methylbenzoate). A mixture of A-2 (methyl 4-bromo-2-methylbenzoate) (84.65 g, 369.5 mmol) and cuprous cyanide (45 g, 502.5 mmol) in dimethylformamide (60 mL) was refluxed for 8 h. After being cooled down to room temperature, the reaction mixture was diluted with water (400 mL), and the resulting mixture was filtrated. The filter cake was washed with ethyl acetate (200 mL×3). The filtrate was washed with water (400 mL), and the aqueous layer was extracted with ethyl acetate (200 mL×2). The combined organic layer was washed with brine (400 mL), dried over anhydrous sodium sulfate (40 g), and evaporated. The residue was purified by silica gel column chromatography (petroleum ether/ethyl acetate=15:1) to afford A-3, (methyl 4-cyano-2-methylbenzoate) (38 g, yield 58.7%) as a yellow solid. $^1$H NMR (CDCl$_3$ 400 MHz): δ 8.05 (d, J=39.6 Hz, 1H), 7.56(d, J=8.0 Hz, 2H), 3.96 (s, 3H), 2.65 (s, 3H).

Synthesis of A-4, (4-cyano-2-methylbenzoic acid). To a solution of A-3 (methyl 4-cyano-2-methylbenzoate) (38 g, 0.217 mol) in ethanol (450 mL) was added aqueous sodium hydroxide solution (150 mL, 2.9 M), and the mixture was stirred at room temperature for 12 h. Most of ethanol was removed under reduced pressure, and the residue was diluted with water (300 mL). The aqueous layer was washed with ethyl ether (200 mL×2), and the aqueous layer was acidified with hydrochloric acid (450 mL, 1 M) under 0° C. to pH<6. The mixture was extracted with ethyl acetate (400 mL×3), and the organic layer was washed with brine, dried, and evaporated to give A-4 (4-cyano-2-methylbenzoic acid) (40 g, yield 100%) as a yellow solid.

Synthesis of A-5, (4-cyano-2-methylbenzoyl chloride). To a solution of A-4 (4-cyano-2-methylbenzoic acid) (20 g, 0.124 mol) in toluene (200 mL) was added thionyl chloride (18 mL, 0.248 mol), and catalytic amount of dimethylformamide (0.5 mL). The resultant mixture was stirred at 70° C. for 14 h, and concentrated under reduced pressure to give A-5 (4-cyano-2-methylbenzoyl chloride) (24 g, yield 100%), which was used in the next step without further purification.

Synthesis of A-6, (ethyl 3-(4-cyano-2-methylphenyl)-2-(4-methoxyphenyl)-3-oxopropanoate). To a solution of (4-methoxy-phenyl)-acetic acid ethyl ester (25.96 g, 133.7 mmol) in anhydrous tetrahydrofuran (200 mL) was added lithium hexamethyldisilazide (200 mL, 1 M) at −78° C. under nitrogen. After being stirred for 15 min., a solution of A-5 (4-cyano-2-methylbenzoyl chloride) (24 g, 133.6 mmol) in anhydrous tetrahydrofuran (150 mL) was added dropwise, and the resulting mixture was stirred at room temperature overnight for 16 h. The reaction mixture was quenched by the addition of saturated aqueous ammonium chloride solution (200 mL), and the resultant mixture was extracted with ethyl acetate (100 mL×3). The combined organic layers were dried over anhydrous sodium sulfate (20 g), filtered, and evaporated. The residue was purified on silica gel column (petroleum ether/ethyl acetate=25:1) to give A-6 (ethyl 3-(4-cyano-2-methylphenyl)-2-(4-methoxyphenyl)-3-oxopropanoate) (40 g, yield 88.7%).

Synthesis of A-7, (4-(2-(4-methoxyphenyl)acetyl)-3-methylbenzonitrile). To a mixture of ethyl 3-(4-cyano-2-methylphenyl)-2-(4-methoxyphenyl)-3-oxopropanoate (A-6) (40 g, 0.1186 mol) in dimethyl sulfoxide (75 mL) was added catalytic amount of brine (2.5 mL), and the reaction mixture was heated at 150° C. for 2.5 h. When TLC showed the starting material was consumed, the reaction mixture was cooled down to room temperature, and partitioned between water (150 mL) and ethyl acetate (150 mL). The aqueous layer was extracted with ethyl acetate (100 mL×2). The combined organic layer was washed with brine (200 mL), dried over anhydrous sodium sulfate (15 g), evaporated, and purified by chromatography on silica gel (petroleum ether/ethyl acetate=25:1) to give 4-(2-(4-methoxyphenyl)acetyl)-3-methylbenzonitrile (A-7) (19 g, yield 60.4%).

Synthesis of A-8, (4-(2-(4-methoxyphenyl)pent-4-enoyl)-3-methylbenzonitrile). To a solution of A-7 (4-(2-(4-methoxyphenyl)acetyl)-3-methylbenzonitrile) (19 g, 71.6 mmol) in anhydrous tetrahydrofuran (200 mL) was added dropwise lithium hexamethyldisilazide (LiHMDS) (86 mL, 1 mol/L in THF) at −78° C. under nitrogen, and the reaction mixture was stirred at −78° C. for 30 min. A solution of 3-bromo-propene (10.4 g, 86 mmol) in anhydrous tetrahydrofuran (70 mL) was added dropwise into the mixture, and the resulting mixture was warmed to room temperature and stirred overnight. The reaction was quenched by the addition of saturated aqueous ammonium chloride solution (200 mL), and extracted with ethyl acetate (100 mL×3). The combined organic layers were washed with brine (200 mL), dried over anhydrous sodium sulfate (10 g), evaporated, and purified on silica gel column (petroleum ether/ethyl acetate=25:1) to give A-8 (4-(2-(4-methoxyphenyl)pent-4-enoyl)-3-methylbenzonitrile) (7.7 g, yield 35.2%) as an oil. $^1$H NMR (CDCl$_3$ 400 MHZ): δ 7.36 (m, 3H), 7.01 (d, J=8.4 Hz, 2H), 6.74 (d, J=8.4 Hz, 2H), 5.72-5.62 (m, 1H), 5.04-4.93 (m, 2H), 4.20-4.17 (m, 1H), 3.69 (s, 3H), 2.92-2.85 (m, 1H), 2.52-2.40 (m, 1H), 2.16 (s, 3H).

Synthesis of Intermediate A, (4-(2-(4-methoxyphenyl)-4-oxobutanoyl)-3-methylbenzonitrile). To a solution of A-8 (4-(2-(4-methoxyphenyl)pent-4-enoyl)-3-methylbenzonitrile) (9.1 g, 29.8 mmol) in dichloromethane (400 mL) at −78° C. was bubbled with ozone in 40 min. Dimethyl sulfide (20 mL) was slowly added into the solution at −78° C. After the addition, the resulting mixture was stirred at room temperature overnight, poured into water (150 mL), and extracted with dichloromethane (150 mL×2). The organic layer was washed with brine (150 mL), dried over anhydrous sodium sulfate (15 g), evaporated, and purified by silica gel (petroleum ether/ethyl acetate=5:1) to give Intermediate A, 4-(2-(4-methoxyphenyl)-4-oxobutanoyl)-3-methylbenzonitrile (3.0 g, yield 32.8%) as a yellow solid. $^1$H NMR (DMSO-$d_6$ 400 MHZ): δ 9.72 (s, 1H), 7.94 (d, J=8.0 Hz, 1H), 7.77 (d, J=8.0 Hz, 1H), 7.69 (s, 1H), 7.12 (d, J=8.8 Hz, 2H), 6.84 (d, J=8.4 Hz, 2H), 5.00-4.96 (m, 1H), 3.68 (s, 3H), 3.49-3.42 (m, 1H), 2.91-2.85 (m, 1H), 2.11 (s, 3H).

Synthesis of Common Intermediate B, 3-(3-(4-bromophenyl)-2-(4-cyano-2-methylphenyl)-1H-pyrrol-1-yl)propanoic acid

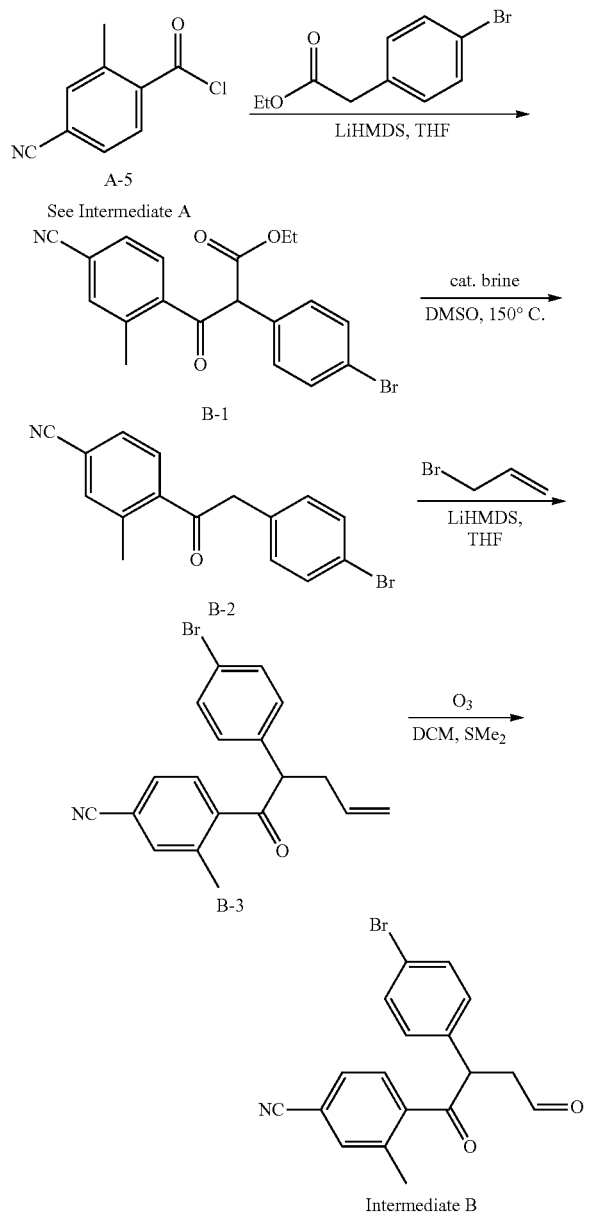

Synthesis of B-1, (ethyl 2-(4-bromophenyl)-3-(4-cyano-2-methylphenyl)-3-oxopropanoate). Followed same procedure as described the synthesis of Intermediate A, step 5 (transformation of A-5 to A-6) using ethyl 2-(4-bromophenyl)acetate.

Synthesis of B-2, (4-(2-(4-bromophenyl)acetyl)-3-methylbenzonitrile). To a solution of compound B-1 (8.0 g, 20.7 mmol) in DMSO (50 mL) was added catalytic amount of brine (0.3 mL), and the reaction mixture was heated at 165° C. for 2 h. When TLC showed the starting material was consumed, the reaction mixture was cooled down to room temperature, and partitioned between water (150 mL) and ethyl acetate (150 mL). The aqueous layer was extracted with ethyl acetate (50 mL×3). The combined organic layer was washed with brine, dried over sodium sulfate, and evaporated to give compound B-2, (4-(2-(4-bromophenyl)acetyl)-3-methylbenzonitrile) (4.5 g, yield: 71%) as a solid.

Synthesis of B-3, 4-(2-(4-bromophenyl)pent-4-enoyl)-3-methylbenzonitrile. Followed same procedure as described the synthesis of Intermediate A, step 7 (transformation of A-7 to A-8). Purification of the crude was accomplished via silica gel column (eluting with 10% ethyl acetate in petroleum ether) to give B-3, 4-(2-(4-bromophenyl)pent-4-enoyl)-3-methylbenzonitrile (yield: 41%) as oil.

Synthesis of Intermediate B, 4-(2-(4-bromophenyl)-4-oxobutanoyl)-3-methylbenzonitrile. A solution of compound B-3 (2.0 g, 7.6 mmol) in DCM (100 mL) was bubbled with $O_3$ at −78° C. for 1 h. After the reaction mixture was warmed to room temperature, it was quenched by the addition of SMe$_2$ (20 mL). Volatiles were evaporated and the residue was purified on silica gel column (petroleum ether:ethyl acetate=3:1) to give Intermediate B, 4-(2-(4-bromophenyl)-4-oxobutanoyl)-3-methylbenzonitrile (700 mg, yield 34.8%) as an oil.

Synthesis of Intermediate C, ethyl 2-(4-cyano-2-methylbenzoyl)-4-oxobutanoate

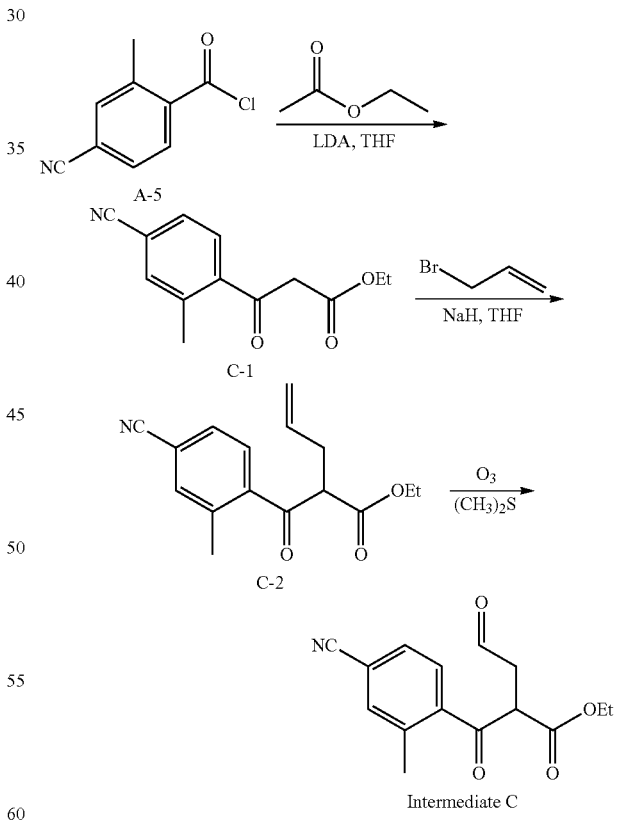

Synthesis of ethyl 3-(4-cyano-2-methylphenyl)-3-oxopropanoate, (C-1). To a solution of diisopropylamine (7.57 g, 75 mmol) in anhydrous THF (150 mL) was added n-BuLi (30 mL, 75 mmol, 2.5 M in hexane) at −78° C. under nitrogen, after being stirred for 15 min., a solution of ethyl acetate (6.33 g, 72 mmol) in anhydrous THF (20 mL) was added dropwise.

The resulting mixture was stirred for an additional one hour, and a solution of compound A-5 (see synthesis of Intermediate A) in THF (50 mL) was added dropwise. After the addition, the resulting mixture was stirred at room temperature overnight. The reaction mixture was quenched by saturated aqueous NH₄Cl solution (200 mL), and the resultant mixture was extracted with ethyl acetate (100 mL×3). The combined organic layers were dried over Na₂SO₄, filtered, and evaporated under vacuum. The residue was purified on silica gel column (eluting with 5-8% ethyl acetate in petroleum ether) to give compound C-1 (4.1 g, yield: 30%).

Synthesis of ethyl 2-(4-cyano-2-methylbenzoyl)pent-4-enoate, (C-2). To a solution of compound C-1 (4.1 g, 17.7 mmol) in anhydrous THF (60 mL) at 0° C. under nitrogen was added NaH (60% in mineral, 1.0 g, 25 mmol) in portions, after the addition, the reaction mixture was stirred at 0° C. for 30 min. A solution of 3-bromo-propene (2.68 mg, 22.2 mmol) in anhydrous THF (20 mL) was added dropwise into the mixture, and the resulting mixture was refluxed overnight. After being cooled down to room temperature, the reaction mixture was quenched by the addition of saturated ammonium chloride solution (100 mL), and the resulting mixture was extracted with ethyl acetate (50 mL×3). The combined organic layer was washed with brine, dried over sodium sulfate, and evaporated. The residue was purified on silica gel column (eluting with 10% ethyl acetate in petroleum ether) to give compound C-2 (2.8 g, yield: 58%) as an oil.

Synthesis of ethyl 2-(4-cyano-2-methylbenzoyl)-4-oxobutanoate, (Intermediate C). A solution of compound C-2 (2.8 g, 10.3 mmol) in DCM (60 mL) was bubbled with O₃ for 1 h at −78° C., after the reaction mixture was warmed to room temperature, it was quenched by the addition of SMe₂ (5 mL). Volatiles were evaporated, and the residue was purified on silica gel column (eluting with 30% ethyl acetate in petroleum ether) to give Intermediate C (1.5 g, yield: 53%) as an oil.

Synthesis of Intermediate D, ethyl 2-(4-bromo-2-methylbenzoyl)-4-oxobutanoate

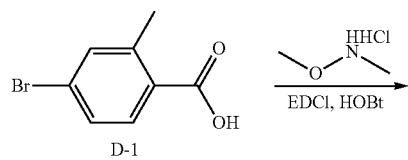

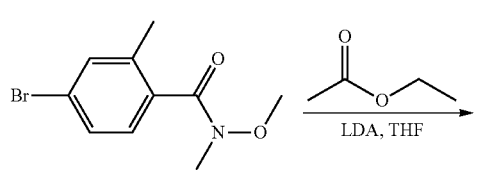

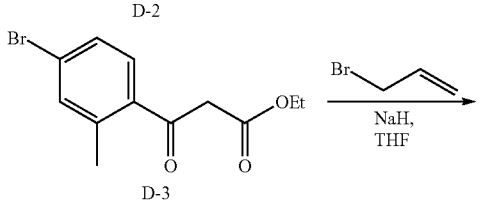

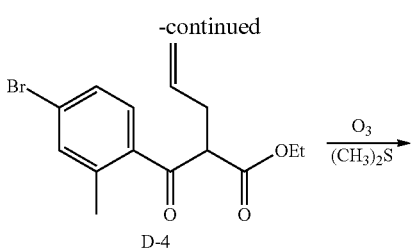

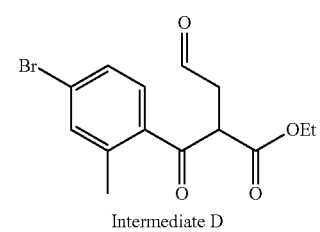

Intermediate D

Synthesis of 4-bromo-N-methoxy-N,2-dimethylbenzamide, (D-2). To the solution of compound 4-bromo-2-methylbenzoic acid D-1 (50 g, 0.23 mol) in DCM (500 mL) was added EDCI (48 g, 0.25 mol), HOBt (34.1 g, 0.25 mol), NMM (50.5 g, 0.50 mol) and N,O-dimethylhydroxylamine hydrochloride (24.3 g, 0.25 mol). The reaction mixture was stirred at room temperature overnight, diluted with DCM, washed with H₂O (300 mL), 1 N HCl (300 mL), and saturated sodium bicarbonate solution (300 mL), dried over sodium sulfate, and concentrated to give the desired product D-2 (55 g, yield 91.6%) as yellow oil.

Synthesis of ethyl 3-(4-bromo-2-methylphenyl)-3-oxopropanoate, (D-3). Followed similar procedure to that described in the synthesis of C-1, of Intermediate C synthesis. The only deviation was that the reaction was allowed to stir 4 hours at −78° C. after final addition before warming to room temperature.

Synthesis of ethyl 2-(4-bromo-2-methylbenzoyl)pent-4-enoate, (D-4). Followed the procedure described in the synthesis of C-2, of Intermediate C synthesis.

Synthesis of ethyl 2-(4-bromo-2-methylbenzoyl)-4-oxobutanoate, Intermediate D. Followed the procedure described in the final step of the synthesis of Intermediate C.

Scheme 1: A general scheme for preparing GSNOR inhibitors with structure 1-2

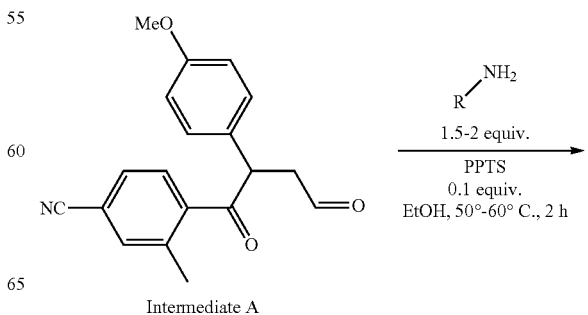

Intermediate A

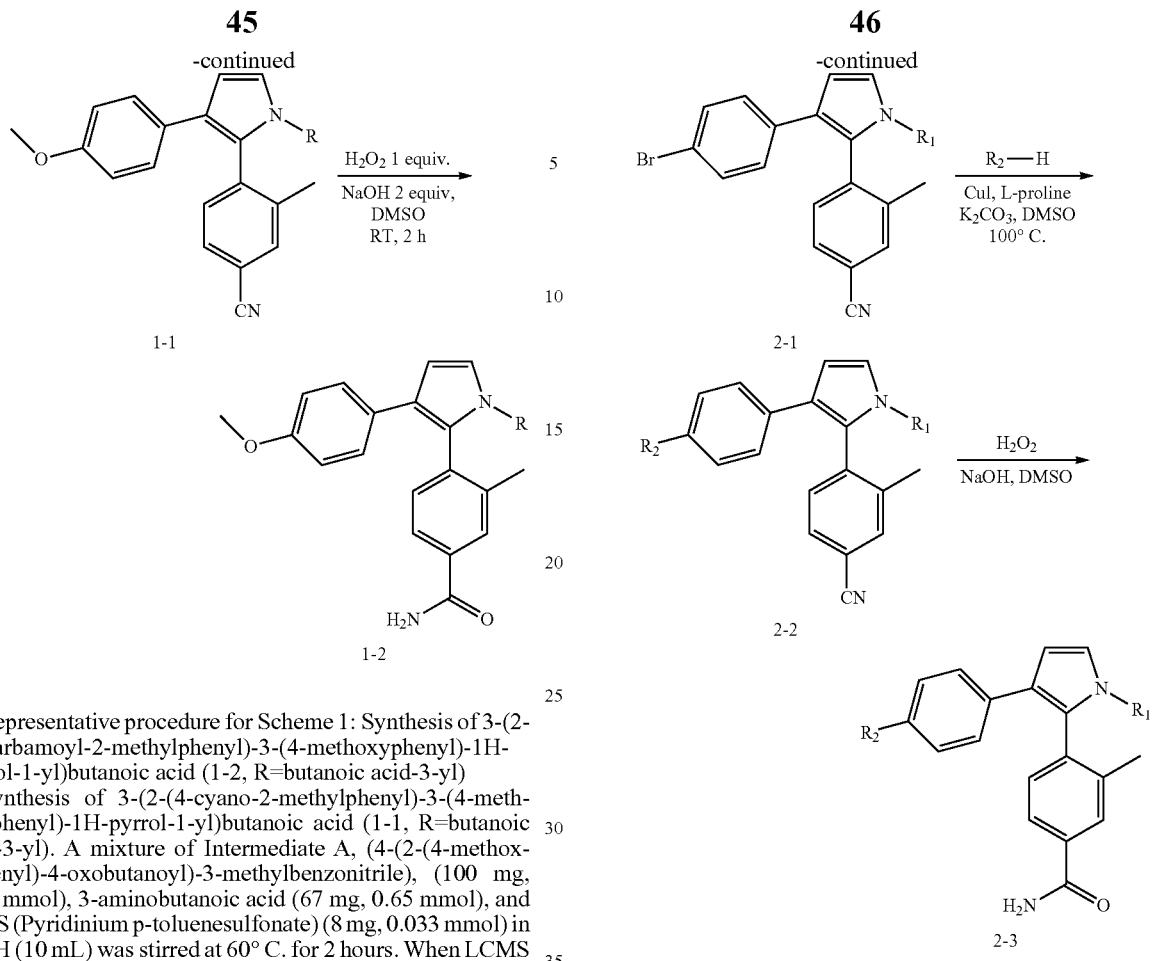

1-1

1-2

Representative procedure for Scheme 1: Synthesis of 3-(2-(4-carbamoyl-2-methylphenyl)-3-(4-methoxyphenyl)-1H-pyrrol-1-yl)butanoic acid (1-2, R=butanoic acid-3-yl)

Synthesis of 3-(2-(4-cyano-2-methylphenyl)-3-(4-methoxyphenyl)-1H-pyrrol-1-yl)butanoic acid (1-1, R=butanoic acid-3-yl). A mixture of Intermediate A, (4-(2-(4-methoxyphenyl)-4-oxobutanoyl)-3-methylbenzonitrile), (100 mg, 0.33 mmol), 3-aminobutanoic acid (67 mg, 0.65 mmol), and PPTS (Pyridinium p-toluenesulfonate) (8 mg, 0.033 mmol) in EtOH (10 mL) was stirred at 60° C. for 2 hours. When LCMS indicated that Intermediate A was consumed, the mixture was concentrated in vacuo to afford the crude desired compound 3-(2-(4-cyano-2-methylphenyl)-3-(4-methoxyphenyl)-1H-pyrrol-1-yl)butanoic acid (120 mg), which was used directly in the next step.

Synthesis of 3-(2-(4-carbamoyl-2-methylphenyl)-3-(4-methoxyphenyl)-1H-pyrrol-1-yl)butanoic acid (1-2, R=butanoic acid-3-yl). To a solution of the crude 3-(2-(4-cyano-2-methylphenyl)-3-(4-methoxyphenyl)-1H-pyrrol-1-yl)butanoic acid (120 mg) in DMSO (5 mL) was added a solution NaOH (26 mg, 0.65 mmol) in a mixture of water (0.5 mL) and $H_2O_2$ (0.33 mmol). After being stirred at room temperature for 2 hours, the mixture was purified by preparative HPLC to give 26 mg of 3-(2-(4-carbamoyl-2-methylphenyl)-3-(4-methoxyphenyl)-1H-pyrrol-1-yl)butanoic acid (yield 20% in two steps) as a grey solid.

Scheme 2: A general scheme for preparing GSNOR inhibitors with structure 2-3.

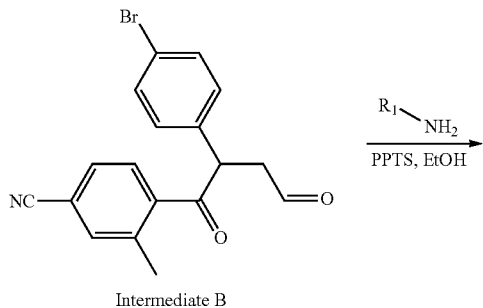

Intermediate B 2-1

2-2

2-3

Representative procedure for Scheme 2: Synthesis of 3-(3-(4-(1H-imidazol-1-yl)phenyl)-2-(4-carbamoyl-2-methylphenyl)-1H-pyrrol-1-yl)propanoic acid Synthesis of 3-(3-(4-bromophenyl)-2-(4-cyano-2-methylphenyl)-1H-pyrrol-1-yl)propanoic acid (2-1, R1=propanoic acid-3-yl). A mixture of Intermediate B (600 mg, 1.685 mmol), 3-amino-propionic acid (300 mg, 3.37 mmol), PPTS (41.4 mg, 0.168 mmol) in anhydrous ethanol (25 mL) was stirred at room temperature overnight. The reaction mixture was evaporated, and the residue was purified on silica gel column (eluting with 1% to 2% methanol in dichloromethane) to give 3-(3-(4-bromophenyl)-2-(4-cyano-2-methylphenyl)-1H-pyrrol-1-yl)propanoic acid (400 mg, yield 58.3%)

Synthesis of 3-(3-(4-(1H-imidazol-1-yl)phenyl)-2-(4-cyano-2-methylphenyl)-1H-pyrrol-1-yl)propanoic acid (2-2, R1=propanoic acid-3-yl, R2=1H-imidazol-1-yl). To a mixture of 3-(3-(4-bromophenyl)-2-(4-cyano-2-methylphenyl)-1H-pyrrol-1-yl)propanoic acid (400 mg, 0.98 mmol) and imidazole (200 mg, 2.94 mol) in DMSO (5 mL) was added L-proline (33.8 mg, 0.294 mmol), CuI (111.7 mg, 0.588 mmol) and K2CO3 (270 mg, 1.96 mmol), then the resultant mixture was stirred at 100° C. overnight. After being cooled down to room temperature, the reaction mixture was filtered, and the filter cake was washed with ethyl acetate (10 mL×3). The combined filtrate was washed with saturated NaHCO3 aqueous solution (30 mL), and the aqueous layer was extracted with ethyl acetate (15 mL×3). The combined organic layers were washed with brine, dried over MgSO4, concentrated. The residue was purified by silica gel column (DCM: MeOH=30:1-20:1) to afford 3-(3-(4-(1H-imidazol-1- yl)phenyl)-2-(4-cyano-2-methylphenyl)-1H-pyrrol-1-yl)propanoic acid (190 mg, yield 48.9%) as a solid.

Synthesis of 3-(3-(4-(1H-imidazol-1-yl)phenyl)-2-(4-carbamoyl-2-methylphenyl)-1H-pyrrol-1-yl)propanoic acid (2-3, R1=propanoic acid-3-yl, R2=1H-imidazol-1-yl). To a mixture of compound 3-(3-(4-(1H-imidazol-1-yl)phenyl)-2-(4-cyano-2-methylphenyl)-1H-pyrrol-1-yl)propanoic acid (180 mg, 0.98 mmol) and sodium hydroxide (80 mg, 2.0 mol) in DMSO (5 mL) was added 0.1 mL of 30% hydrogen peroxide, and the mixture was stirred at room temperature overnight. The reaction mixture was neutralized by 1N HCl to PH=5-6, concentrated, and purified by preparative HPLC to give 3-(3-(4-(1H-imidazol-1-yl)phenyl)-2-(4-carbamoyl-2-methylphenyl)-1H-pyrrol-1-yl)propanoic acid (29 mg, yield 15.4%) as a solid.

Scheme 2A: Synthesis of 4-(1-(3-fluoro-4-hydroxyphenyl)-3-(4-(2-methyl-1H-imidazol-1-yl)phenyl)-1H-pyrrol-2-yl)-3-methylbenzamide (Scheme 2 with modification).

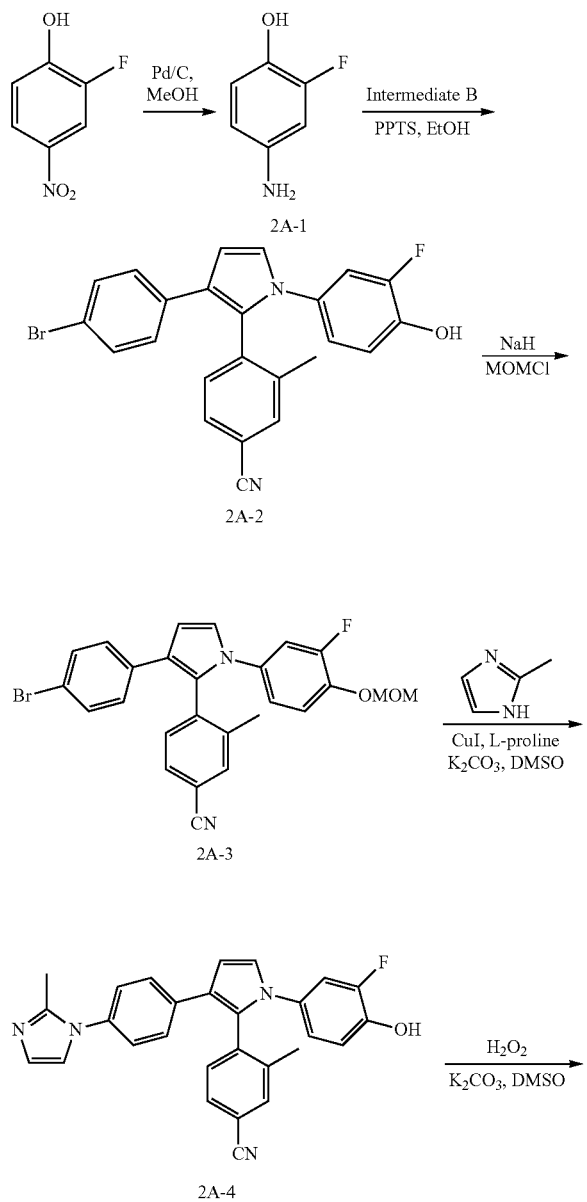

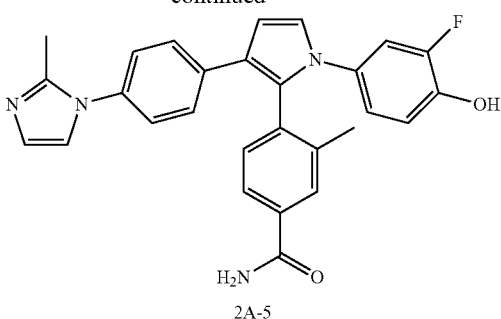

Synthesis of 4-amino-2-fluorophenol (2A-1). Under $H_2$, a mixture of 2-fluoro-4-nitrophenol (10 g, 63.7 mmol) and Pd/C (1 g) in methanol (100 mL) was stirred at room temperature for 5 hours. The mixture was filtered, and concentrated in vacuo to give the compound 2A-1 (7 g, yield 86%).

Synthesis of 4-(3-(4-bromophenyl)-1-(3-fluoro-4-hydroxyphenyl)-1H-pyrrol-2-yl)-3-methylbenzonitrile (2A-2). Followed same procedure as described above in step 1 of Scheme 2.

Synthesis of 4-(3-(4-bromophenyl)-1-(3-fluoro-4-(methoxymethoxy)phenyl)-1H-pyrrol-2-yl)-3-methylbenzonitrile (2A-3). To a mixture of compound 2A-2 (400 mg, 0.89 mmol) in DMF (5 mL) was added NaH (54 mg, 1.34 mmol) at 0° C., and the mixture was stirred for 1 hour. To the mixture, MOMCl (108 mg, 1.34 mmol) was added, and the mixture was stirred for 1 hour. The mixture was quenched with water slowly, and extracted with ethyl acetate (50 mL×3). The combined organic layers were washed with brine, dried over $Na_2SO_4$, and concentrated to give the compound 2A-3 (370 mg, yield 84%).

Synthesis of 4-(1-(3-fluoro-4-hydroxyphenyl)-3-(4-(2-methyl-1H-imidazol-1-yl)phenyl)-1H-pyrrol-2-yl)-3-methylbenzonitrile (2A-4). Followed procedure described in step 2 of Scheme 2, where the reaction mixture was heated to 140° C. for 6 hours, workup was as described, and purification was by silica gel column (PE:EA=5:1-1:1) to afford the compound 2A-4 (160 mg, yield 50%).

Synthesis of 4-(1-(3-fluoro-4-hydroxyphenyl)-3-(4-(2-methyl-1H-imidazol-1-yl)phenyl)-1H-pyrrol-2-yl)-3-methylbenzamide (2A-5). Followed procedure described in step 3 of Scheme 2, except for purification which was achieved by thin layer chromatography ($CH_2Cl_2$:MeOH=10:1) to give 2A-5 (16.3 mg, yield 15.4%).

Scheme 3: A general scheme for preparing GSNOR inhibitors with structure 3-7.

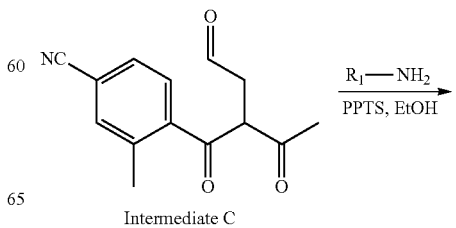

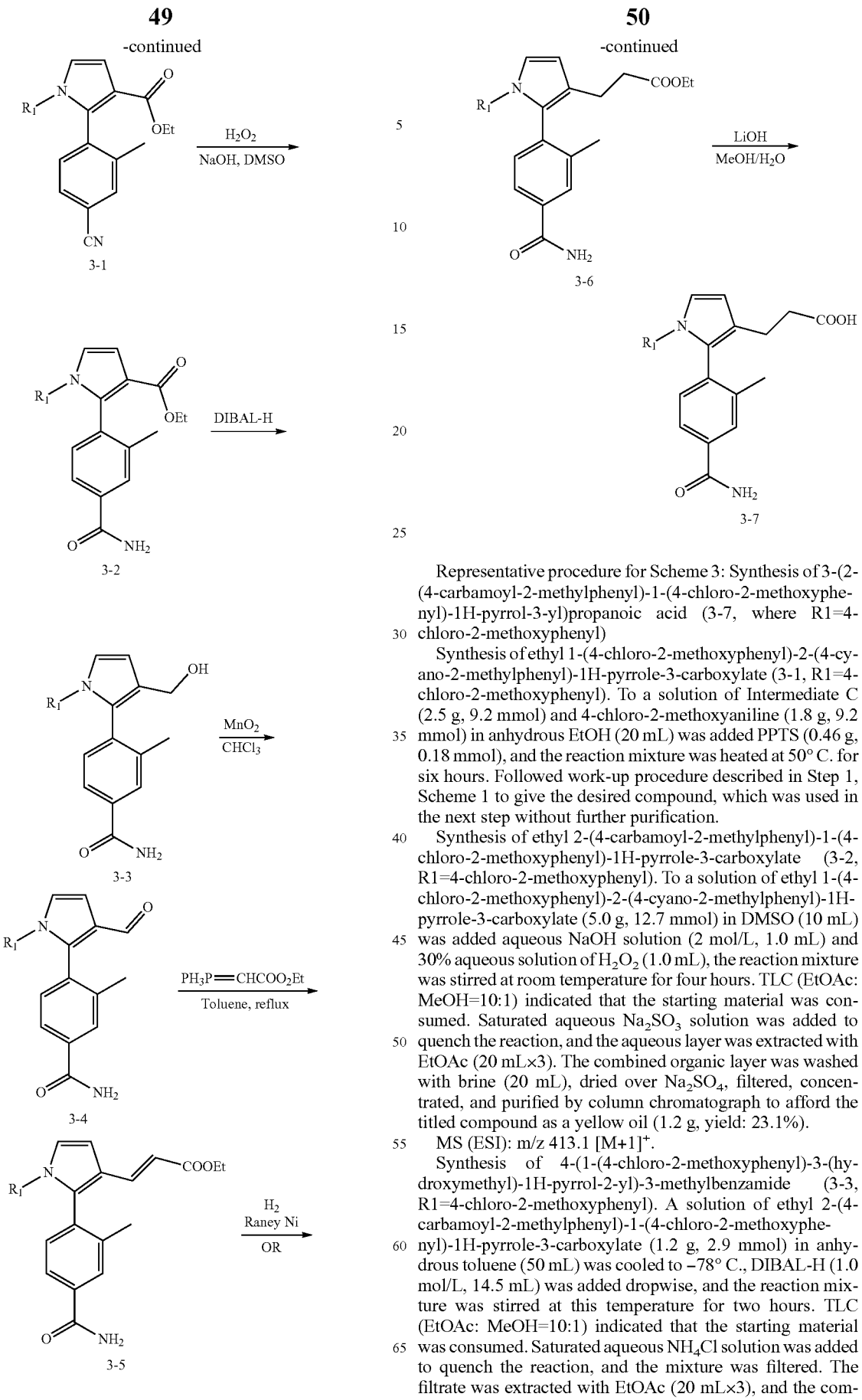

Representative procedure for Scheme 3: Synthesis of 3-(2-(4-carbamoyl-2-methylphenyl)-1-(4-chloro-2-methoxyphenyl)-1H-pyrrol-3-yl)propanoic acid (3-7, where R1=4-chloro-2-methoxyphenyl)

Synthesis of ethyl 1-(4-chloro-2-methoxyphenyl)-2-(4-cyano-2-methylphenyl)-1H-pyrrole-3-carboxylate (3-1, R1=4-chloro-2-methoxyphenyl). To a solution of Intermediate C (2.5 g, 9.2 mmol) and 4-chloro-2-methoxyaniline (1.8 g, 9.2 mmol) in anhydrous EtOH (20 mL) was added PPTS (0.46 g, 0.18 mmol), and the reaction mixture was heated at 50° C. for six hours. Followed work-up procedure described in Step 1, Scheme 1 to give the desired compound, which was used in the next step without further purification.

Synthesis of ethyl 2-(4-carbamoyl-2-methylphenyl)-1-(4-chloro-2-methoxyphenyl)-1H-pyrrole-3-carboxylate (3-2, R1=4-chloro-2-methoxyphenyl). To a solution of ethyl 1-(4-chloro-2-methoxyphenyl)-2-(4-cyano-2-methylphenyl)-1H-pyrrole-3-carboxylate (5.0 g, 12.7 mmol) in DMSO (10 mL) was added aqueous NaOH solution (2 mol/L, 1.0 mL) and 30% aqueous solution of $H_2O_2$ (1.0 mL), the reaction mixture was stirred at room temperature for four hours. TLC (EtOAc:MeOH=10:1) indicated that the starting material was consumed. Saturated aqueous $Na_2SO_3$ solution was added to quench the reaction, and the aqueous layer was extracted with EtOAc (20 mL×3). The combined organic layer was washed with brine (20 mL), dried over $Na_2SO_4$, filtered, concentrated, and purified by column chromatograph to afford the titled compound as a yellow oil (1.2 g, yield: 23.1%).

MS (ESI): m/z 413.1 [M+1]$^+$.

Synthesis of 4-(1-(4-chloro-2-methoxyphenyl)-3-(hydroxymethyl)-1H-pyrrol-2-yl)-3-methylbenzamide (3-3, R1=4-chloro-2-methoxyphenyl). A solution of ethyl 2-(4-carbamoyl-2-methylphenyl)-1-(4-chloro-2-methoxyphenyl)-1H-pyrrole-3-carboxylate (1.2 g, 2.9 mmol) in anhydrous toluene (50 mL) was cooled to −78° C., DIBAL-H (1.0 mol/L, 14.5 mL) was added dropwise, and the reaction mixture was stirred at this temperature for two hours. TLC (EtOAc: MeOH=10:1) indicated that the starting material was consumed. Saturated aqueous $NH_4Cl$ solution was added to quench the reaction, and the mixture was filtered. The filtrate was extracted with EtOAc (20 mL×3), and the combined organic layer was washed with brine (20 mL), dried over Na$_2$SO$_4$, filtered, concentrated, and purified by column chromatography to give the titled compound (430 mg, yield: 40.2%). $^1$H NMR (CD$_3$OD 300 MHz TMS): δ 7.63 (s, 1H), 7.55 (m, 1H), 7.21 (d, J=7.8 Hz, 1H), 7.03 (d, J=8.1 Hz, 1H), 6.95 (d, J=2.1 Hz, 1H), 6.82-6.87 (m, 2H), 6.43 (d, J=3.0 Hz, 1H), 4.38 (d, J=11.7 Hz, 1H), 4.27 (d, J=11.7 Hz, 1H), 3.60 (s, 3H), 2.10 (s, 3H).

Synthesis of 4-(1-(4-chloro-2-methoxyphenyl)-3-formyl-1H-pyrrol-2-yl)-3-methylbenzamide, (3-4, R1=4-chloro-2-methoxyphenyl). To a solution of 4-(1-(4-chloro-2-methoxyphenyl)-3-(hydroxymethyl)-1H-pyrrol-2-yl)-3-methylbenzamide (430 mg, 1.2 mmol) in CH$_2$Cl$_2$ (10 mL) was added MnO$_2$ (562 mg, 6.5 mmol), the reaction mixture was refluxed for two days. TLC (EtOAc: MeOH=10:1) indicated that the starting materials were consumed. The reaction mixture was filtered, and the filtrate was concentrated to give the desired compound (320 mg, yield: 75.1%), which was used in the next step without further purification.

Synthesis of (E)-ethyl 3-(2-(4-carbamoyl-2-methylphenyl)-1-(4-chloro-2-methoxyphenyl)-1H-pyrrol-3-yl)acrylate, (3-5, R1=4-chloro-2-methoxyphenyl). To a solution of 4-(1-(4-chloro-2-methoxyphenyl)-3-formyl-1H-pyrrol-2-yl)-3-methylbenzamide (320 mg, 0.87 mmol) in anhydrous toluene (10 mL) was added compound Ph$_3$P=CHCO$_2$Et (440 mg, 1.3 mmol), and the reaction mixture was refluxed overnight. The solvent was removed in vacuo, and the residue was purified by column chromatography (eluting with ethyl acetate in petroleum ether) to give the crude compound (E)-ethyl 3-(2-(4-carbamoyl-2-methylphenyl)-1-(4-chloro-2-methoxyphenyl)-1H-pyrrol-3-yl)acrylate (610 mg), which contents some of Ph$_3$PO. $^1$H NMR (CD$_3$OD 400 MHz TMS): δ 7.54-7.72 (m, 2H), 7.25 (d, J=15.6 Hz, 1H), 7.12-7.20 (m, 2H), 7.00 (s, 1H), 6.87-6.92 (m, 2H), 6.70 (d, J=3.2 Hz, 1H), 6.25 (d, J=15.6 Hz, 1H), 4.15 (q, J=7.2 Hz, 2H), 3.63 (s, 3H), 2.12 (s, 3H), 1.25 (t, J=7.2 Hz, 3H).

Synthesis of ethyl 3-(2-(4-carbamoyl-2-methylphenyl)-1-(4-chloro-2-methoxyphenyl)-1H-pyrrol-3-yl)propanoate, (3-6, R1=4-chloro-2-methoxyphenyl). To a solution of (E)-ethyl 3-(2-(4-carbamoyl-2-methylphenyl)-1-(4-chloro-2-methoxyphenyl)-1H-pyrrol-3-yl)acrylate (610 mg, 1.4 mmol) in THF (10 mL) was added Raney Ni (100 mg), and the reaction mixture was hydrogenated at room temperature under 1 atm of hydrogen for two hours. The reaction mixture was filtered, and the filtrate was concentrated to give the title compound (610 mg), which was used in the next step without further purification.

Synthesis of 3-(2-(4-carbamoyl-2-methylphenyl)-1-(4-chloro-2-methoxyphenyl)-1H-pyrrol-3-yl)propanoic acid, (3-7, R1=4-chloro-2-methoxyphenyl). To a solution of ethyl 3-(2-(4-carbamoyl-2-methylphenyl)-1-(4-chloro-2-methoxyphenyl)-1H-pyrrol-3-yl)propanoate (580 mg, 1.3 mmol) in MeOH (5 mL) was added aqueous LiOH solution (2 mol/L, 5 mL), and the reaction mixture was stirred at room temperature for three hours. TLC (PE: EtOAc=1:2) showed that the starting material was consumed. The aqueous layer was washed with EtOAc (10 mL), and acidified by 0.5 N HCl to pH=2. The aqueous layer was extracted with a mixture of EtOAc and MeOH (v/v=10:1, 20 mL×3), and the combined organic layer was washed with brine (20 mL), dried over Na$_2$SO$_4$, filtered, and concentrated. The residue was purified by column chromatography and preparative HPLC to afford the titled compound as an off-white solid (68.3 mg, yield: 12.6%).

Scheme 4: A general scheme for preparing GSNOR inhibitors with structure 4-2.

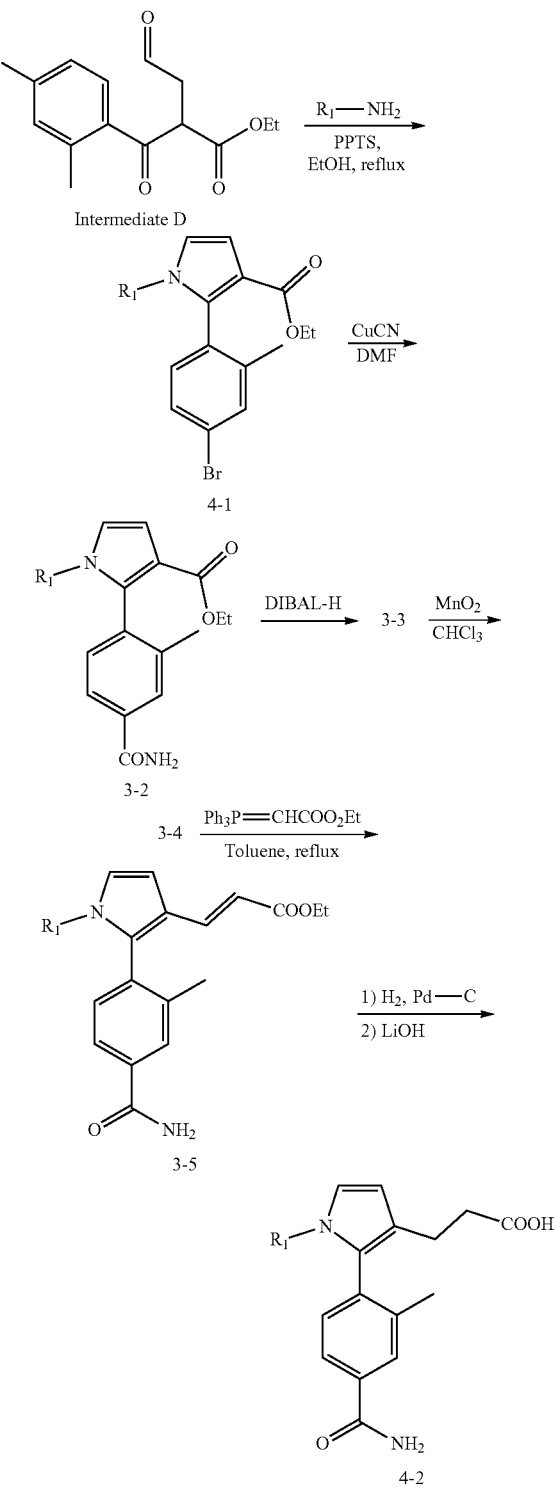

Representative procedure for Scheme 4: Synthesis of 3-(2-(4-carbamoyl-2-methylphenyl)-1-(4-methoxyphenyl)-1H-pyrrol-3-yl)propanoic acid (4-2, R1=4-methoxyphenyl).

Synthesis of ethyl 2-(4-bromo-2-methylphenyl)-1-(4-methoxyphenyl)-1H-pyrrole-3-carboxylate (4-1, R1=4-methoxyphenyl). A mixture of Intermediate D (5 g, 15.3 mmol), 4-methoxy-phenylamine (1.9 mg, 15.3 mmol), PPTS (140 mg, 0.57 mmol) in anhydrous ethanol (100 mL) was stirred at room temperature overnight. The reaction mixture was evaporated, and purified by silica gel column (eluting with 20% ethyl acetate in petroleum ether) to give the desired compound (1 g, yield 15.7%) as a solid.

Synthesis of ethyl 2-(4-carbamoyl-2-methylphenyl)-1-(4-methoxyphenyl)-1H-pyrrole-3-carboxylate (3-2, R1=4-methoxyphenyl). To a mixture of ethyl 2-(4-bromo-2-methylphenyl)-1-(4-methoxyphenyl)-1H-pyrrole-3-carboxylate (1 g, 2.4 mmol) in DMF (50 mL) was added CuCN (0.43 g, 4.8 mmol), and the suspension solution was heated to 180° C. for 12 h. After being cooled down to room temperature, the reaction mixture was poured into water, and the mixture was extracted with ethyl acetate (50 mL×3). The combined organic layers were washed with brine, dried over Na$_2$SO$_4$, and concentrated under reduced pressure. The residue was purified on silica gel column chromatography (eluting with 50% ethyl acetate in petroleum ether) to give the title compound (600 mg, 66% yield) as a white solid.

Synthesis of ethyl 2-(4-carbamoyl-2-methylphenyl)-1-(4-methoxyphenyl)-1H-pyrrole-3-carboxylate (3-5, R1=4-methoxyphenyl). Transformation of ethyl 2-(4-carbamoyl-2-methylphenyl)-1-(4-methoxyphenyl)-1H-pyrrole-3-carboxylate (3-2, R1=4-methoxyphenyl) to the desired ethyl 2-(4-carbamoyl-2-methylphenyl)-1-(4-methoxyphenyl)-1H-pyrrole-3-carboxylate (3-5, R1=4-methoxyphenyl) followed the same 3 steps described in the example synthesis for Scheme 3, (3-2→3-3→3-4→3-5).

Synthesis of 3-(2-(4-carbamoyl-2-methylphenyl)-1-(4-methoxyphenyl)-1H-pyrrol-3-yl)propanoic acid (4-2, R1=4-methoxyphenyl). To a mixture of ethyl 2-(4-carbamoyl-2-methylphenyl)-1-(4-methoxyphenyl)-1H-pyrrole-3-carboxylate (240 mg, 0.4 mmol) in methanol (10 mL) was added 10% palladium on activated carbon (50 mg), and the mixture was hydrogenated under 1 atm of hydrogen at room temperature over 2 h. The reaction mixture was filtrated, concentrated under reduced pressure, and dissolved in a mixture of ethanol (10 mL) and 1N NaOH solution (5 mL). The resulting mixture was stirred at room temperature overnight, the organic solvent was evaporated, and the mixture was adjusted to pH=3 with 1N HCl. The aqueous layer was extracted with EtOAc (10 mL×3), and the organic layers were washed with brine, dried over sodium sulfate, concentrated under reduced pressure, and purified by preparative HPLC to give the title compound (75 mg, yield: 30% in two steps).

Scheme 5: A general scheme for preparing GSNOR inhibitors with structure 5-4.

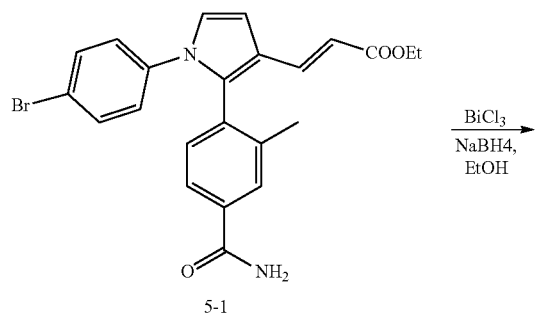

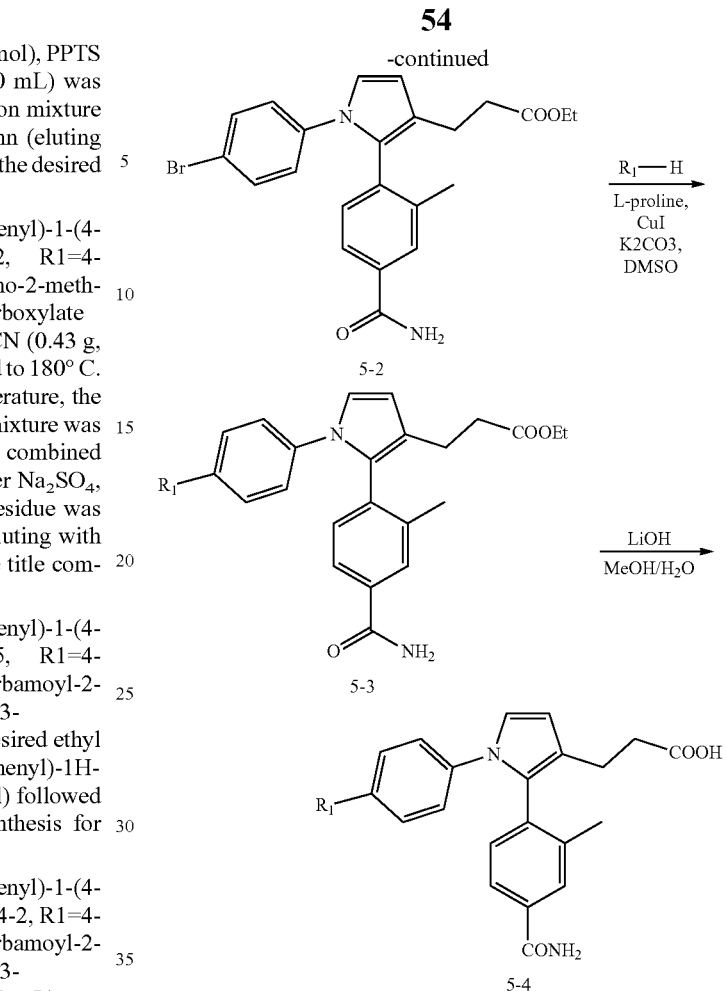

Representative procedure for Scheme 5: Synthesis of 3-(1-(4-(1H-imidazol-1-yl)phenyl)-2-(4-carbamoyl-2-methylphenyl)-1H-pyrrol-3-yl)propanoic acid (5-4, R1=1H-imidazol-1-yl)

Synthesis of (E)-ethyl 3-(1-(4-bromophenyl)-2-(4-carbamoyl-2-methylphenyl)-1H-pyrrol-3-ypacrylate (5-1). Described in Scheme 3, compound 3-5, where R1=4-bromophenyl Synthesis of ethyl 3-(1-(4-bromophenyl)-2-(4-carbamoyl-2-methylphenyl)-1H-pyrrol-3-yl)propanoate (5-2). To an ice cooled solution of (E)-ethyl 3-(1-(4-bromophenyl)-2-(4-carbamoyl-2-methylphenyl)-1H-pyrrol-3-yl)acrylate (400 mg, 0.88 mmol) in 95% ethanol (10 mL) were added BiCl$_3$ (554 mg, 1.76 mmol) and portionwise NaBH$_4$ (134 mg, 3.52 mmol), then the resultant mixture was stirred at room temperature for 12 h. The reaction mixture was filtered, and the filtrate was partitioned between water (50 mL) and ethyl acetate (30 mL), the aqueous layer was extracted with ethyl acetate (30 mL×2). The combined organic layers were washed with brine, dried over sodium sulfate, and evaporated. The residue was purified by preparative TLC (eluting with 50% ethyl acetate in petroleum ether for three times) to give ethyl 3-(1-(4-bromophenyl)-2-(4-carbamoyl-2-methylphenyl)-1H-pyrrol-3-yl)propanoate (5-2) (100 mg, yield: 25%).

Synthesis of ethyl 3-(1-(4-(1H-imidazol-1-yl)phenyl)-2-(4-carbamoyl-2-methylphenyl)-1H-pyrrol-3-yl)propanoate, (5-3, R1=1H-imidazol-1-yl). A mixture of ethyl 3-(1-(4-bromophenyl)-2-(4-carbamoyl-2-methylphenyl)-1H-pyrrol-3-yl)propanoate (50 mg, 0.11 mmol), imidazole (68 mg, 10 mmol), L-proline (13 mg, 0.11 mmol), CuI (42 mg, 0.22 mmol), K$_2$CO$_3$ (76 mg, 0.55 mmol) and 4 Å molecular sieve (100 mg) in DMSO (3 mL) was heated at 130° C. for 24 h. After being cooled down to room temperature, the reaction mixture was filtered, and the filter cake was washed with ethyl acetate (10 mL×3). The combined filtrate was washed with saturated NaHCO$_3$ aqueous solution (30 mL), and the aqueous layer was extracted with ethyl acetate (15 mL×3). The combined organic layers were washed with brine, dried over MgSO$_4$, and concentrated. The residue was purified by preparative TLC (eluting with 7% methanol in dichloromethane) to give ethyl 3-(1-(4-(1H-imidazol-1-yl)phenyl)-2-(4-carbamoyl-2-methylphenyl)-1H-pyrrol-3-yl)propanoate, (5-3, R1=1H-imidazol-1-yl) (25 mg, yield: 51%), which was used in the next step without further purification.

Synthesis of 3-(1-(4-(1H-imidazol-1-yl)phenyl)-2-(4-carbamoyl-2-methylphenyl)-1H-pyrrol-3-yl)propanoic acid, (5-4, R1=1H-imidazol-1-yl). A mixture of ethyl 3-(1-(4-(1H-imidazol-1-yl)phenyl)-2-(4-carbamoyl-2-methylphenyl)-1H-pyrrol-3-yl)propanoate (25 mg, 0.057 mmol) and LiOH monohydrate (42 mg, 1 mmol) in a mixture of methanol (1.5 mL) and water (0.5 mL), and the reaction mixture was stirred at room temperature overnight. Methanol was removed under reduced pressure, and the residue was diluted with water (5 mL), and the aqueous layer was washed with ethyl acetate (5 mL×3). The aqueous layer was adjusted to PH=6~7 with 1N HCl, and the resulting mixture was extracted with a mixture of dichloromethane and isopropanol (3:1, 5 mL×3). The combined organic layer was dried, and evaporated to give 3-(1-(4-(1H-imidazol-1-yl)phenyl)-2-(4-carbamoyl-2-methylphenyl)-1H-pyrrol-3-yl)propanoic acid, (5-4, R1=1H-imidazol-1-yl) (12 mg, yield: 51%) as a yellow solid.

Scheme 6: Synthesis of 4-(3-(4-methoxyphenyl)-1-(2-(trifluoromethylsulfonamido)ethyl)-1H-pyrrol-2-yl)-3-methylbenzamide

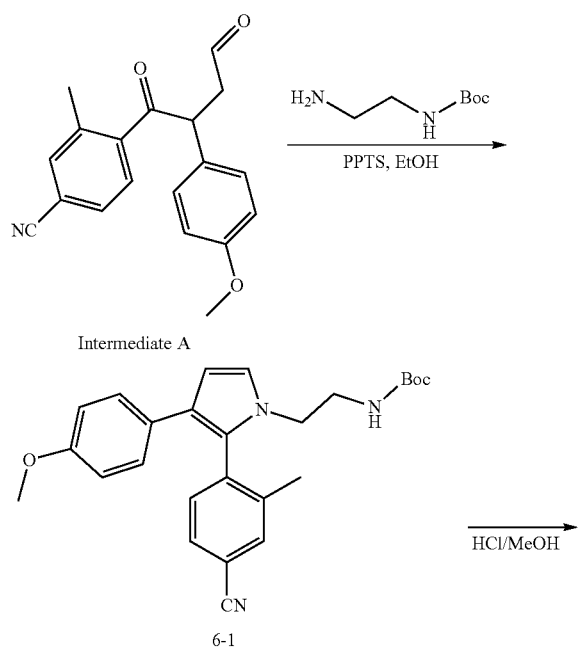

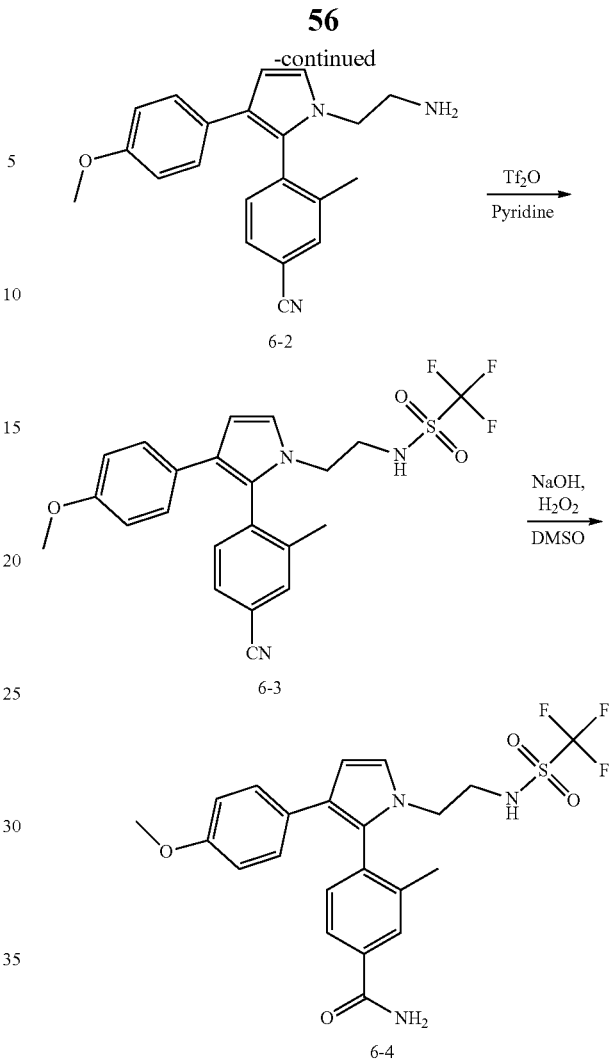

Synthesis of tert-butyl 2-(2-(4-cyano-2-methylphenyl)-3-(4-methoxyphenyl)-1H-pyrrol-1-yl)ethylcarbamate (6-1). Followed procedure described in Step 1 of Scheme 1.

Synthesis of 4-(1-(2-aminoethyl)-3-(4-methoxyphenyl)-1H-pyrrol-2-yl)-3-methylbenzonitrile (6-2). A solution of tert-butyl 2-(2-(4-cyano-2-methylphenyl)-3-(4-methoxyphenyl)-1H-pyrrol-1-yl)ethylcarbamate (6-1) (110 mg, 0.255 mmol) in methanolic hydrochloride solution (2 M, 5 mL) was stirred at room temperature for 1 hour. The mixture was concentrated in vacuo to give the title compound 6-2 (100 mg), which was used directly in the next step.

Synthesis of N-(2-(2-(4-cyano-2-methylphenyl)-3-(4-methoxyphenyl)-1H-pyrrol-1-yl)ethyl)-1,1,1-trifluoromethanesulfonamide (6-3). To a solution of 4-(1-(2-aminoethyl)-3-(4-methoxyphenyl)-1H-pyrrol-2-yl)-3-methylbenzonitrile (6-2) (100 mg, 0.3 mmol) in anhydrous DCM (5 mL) was added pyridine (48 mg, 0.6 mmol), followed by addition of trifluoromethanesulfonic anhydride (85 mg, 0.6 mmol) at 0° C. The mixture was stirred at room temperature overnight. When TLC showed the starting material was consumed, the mixture was partitioned between water and ethyl acetate, and the aqueous layer was extracted with ethyl acetate. The combined organic layer was concentrated under reduced pressure to give the title compound 6-3 (120 mg, yield 86%) as brown oil.

Synthesis of 4-(3-(4-methoxyphenyl)-1-(2-(trifluoromethylsulfonamido)ethyl)-1H-pyrrol-2-yl)-3-methylbenzamide (6-4). Followed step 2 of Scheme 1 to give the desired compound 4-(3-(4-methoxyphenyl)-1-(2-(trifluoromethylsulfonamido)ethyl)-1H-pyrrol-2-yl)-3-methylbenzamide (6-4).

Example 32

GSNOR Assays

Various compounds were tested in vitro for their ability to inhibit GSNOR activity. GSNOR inhibitor compounds in Examples 1-30 had an $IC_{50}$ of about <100 µM. GSNOR inhibitor compounds Examples 1, 3, 5, 6, 9, 13-17, 19-20, 23, 25-27, 29-30 had an $IC_{50}$ of about <5 µM. GSNOR inhibitor compounds Examples 1, 5-6, 13-15, 17, 19, 23, 25, 27, 29-30 had an $IC_{50}$ of about less than 1.0 µM. GSNOR expression and purification is described in *Biochemistry* 2000, 39, 10720-10729.

GSNOR fermentation: Pre-cultures were grown from stabs of a GSNOR glycerol stock in 2XYT media containing 100 ug/ml ampicillin after an overnight incubation at 37° C. Cells were then added to fresh 2XYT (4L) containing ampicillin and grown to an OD ($A_{600}$) of 0.6-0.9 at 37° C. before induction. GSNOR expression was induced with 0.1% arabinose in an overnight incubation at 20° C.

GSNOR Purification: *E. coli* cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR assay: GSNO and Enzyme/NADH Solutions are made up fresh each day. The Solutions are filtered and allowed to warm to room temperature. GSNO Solution: 100 mM NaPO4 (pH 7.4), 0.480 mM GSNO. 396 µL of GSNO Solution is added to a cuvette followed by 8 µL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 µL of each dilution are added to an assay so that the final concentration of DMSO in the assay is 1%. The concentrations of compounds tested range from 100 to 0.003 µM. Enzyme/NADH Solution: 100 mM NaPO4 (pH 7.4), 0.600 mM NADH, 1.0 µg/mL GSNO Reductase. 396 µL of the Enzyme/NADH Solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. IC50's for each compound are calculated using the standard curve analysis in the Enzyme Kinetics Module of SigmaPlot.

Final assay conditions: 100 mM NaPO4, pH 7.4, 0.240 mM GSNO, 0.300 mM NADH, 0.5 µg/mL GSNO Reductase and 1% DMSO. Final volume: 800 µL/cuvette.

Example 33

Efficacy of GSNORi in Experimental Asthma

Experimental Asthma Model:

A mouse model of ovalbumin (OVA)-induced asthma is used to screen GSNOR inhibitors for efficacy against methacholine (MCh)-induced bronchoconstriction/airway hyperreactivity. This is a widely used and well characterized model that presents with an acute, allergic asthma phenotype with similarities to human asthma. Efficacy of GSNOR inhibitors are assessed using a prophylactic protocol in which GSNOR inhibitors are administered prior to challenge with MCh. Bronchoconstriction in response to challenge with increasing doses of MCh is assessed using whole body plethysmography ($P_{enh}$: Buxco). The amount of eosinophil infiltrate into the bronchoaveolar lavage fluid (BALF) is also determined as a measure of lung inflammation. The effect of GSNOR inhibitors are compared to vehicles and to Combivent (inhaled; IH) as the positive control.

Materials and Methods

Allergen Sensitization and Challenge Protocol

OVA (500 µg/ml) in PBS is mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet is resuspended to the original volume in distilled water. Mice receive an intraperitoneal (IP) injection of 100 µg OVA (0.2 mL of 500 µg/mL in normal saline) complexed with alum on day 0. Mice are anesthetized by IP injection of a 0.2-mL mixture of ketamine and xylazine (0.44 and 6.3 mg/mL, respectively) in normal saline and are placed on a board in the supine position. Two hundred fifty micrograms (100 µl of a 2.5 mg/ml) of OVA (on day 8) and 125 µg (50 µl of 2.5 mg/ml) OVA (on days 15, 18, and 21) are placed on the back of the tongue of each animal.

Pulmonary Function Testing (Penh)

In vivo airway responsiveness to methacholine is measured 24 h after the last OVA challenge in conscious, freely moving, spontaneously breathing mice with whole body plethysmography using a Buxco chamber (Wilmington, N.C.). Mice are challenged with aerosolized saline or increasing doses of methacholine (5, 20 and 50 mg/mL) generated by an ultrasonic nebulizer for 2 min. The degree of bronchoconstriction is expressed as enhanced pause ($P_{enh}$), a calculated dimensionless value, which correlates with the measurement of airway resistance, impedance, and intrapleural pressure in the same mouse. $P_{enh}$ readings are taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice are exsanguinated by cardiac puncture, and then BALF is collected from either both lungs or from the right lung after tying off the left lung at the mainstem bronchus. Total BALF cells are counted from a 0.05 mL aliquot, and the remaining fluid is centrifuged at 200×g for 10 min at 4° C. Cell pellets are resuspended in saline containing 10% BSA with smears made on glass slides. Eosinophils are stained for 5 min. with 0.05% aqueous eosin and 5% acetone in distilled water, rinsed with distilled water, and counterstained with 0.07% methylene blue.

GSNOR Inhibitors and Controls

GSNOR inhibitors are reconstituted in phosphate buffered saline (PBS), pH 7.4, at concentrations ranging from 0.00005 to 3 mg/mL. GSNOR inhibitors are administered to mice (10 mL/kg) as a single dose either intravenously (IV) or orally via gavage. Dosing is performed from 30 min. to 24 h prior to MCh challenge. Effect of GSNOR inhibitors are compared to PBS vehicle dosed in the same manner.

Combivent is used as the positive control in all studies. Combivent (Boehringer Ingelheim) is administered to the lung using the inhaler device supplied with the product, but adapted for administration to mice, using a pipet tip. Combivent is administered 48 h, 24 h, and 1 h prior to MCh challenge. Each puff (or dose) of Combivent provides a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge are calculated using GraphPad Prism 5.0 (San Diego, Calif.) and expressed as a percent of the respective (IV or orally administered) vehicle control. Statistical differences among treatment groups and the respective vehicle control group within each study are calculated using one-way ANOVA, Dunnetts (JMP 8.0, SAS Institute, Cary, N.C.). A p value of <0.05 among the treatment groups and the respective vehicle control group is considered significantly different.

It will be apparent to those skilled in the art that various modifications and variations can be made in the methods and compositions of the present invention without departing from the spirit or scope of the invention.

The invention claimed is:

1. The compound of formula I or pharmaceutically acceptable salts thereof:

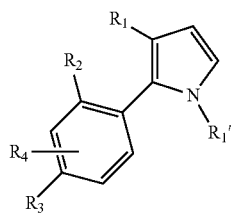

I wherein $R_1$ is selected from the group consisting of $R_5$ and $R_6$;

$R_1'$ is $R_5$ when $R_1$ is $R_6$, and $R_6$ when $R_1$ is $R_5$;

$R_2$ is selected from the group consisting of hydrogen, halogen, hydroxyl, $C_1$-$C_6$ alkyl, $C_3$-$C_6$ cycloalkyl, cyano, nitro, trifluoromethyl, carbamoyl, $C_1$-$C_6$ alkylcarbamoyl, amino, $C_1$-$C_6$ alkylamino, $C_1$-$C_6$ dialkylamino, $C_1$-$C_6$ alkoxyl, and $C_3$-$C_6$ cycloalkoxyl;

$R_3$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, aryl, substituted aryl, heteroaryl, and substituted heteroaryl;

$R_4$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkyl sulfamoyl, amino, $C_1$-$C_6$ alkylamino, $C_1$-$C_6$ dialkylamino, $C_1$-$C_6$ alkoxyl, and $C_3$-$C_6$ cycloalkoxyl;

$R_5$ is selected from the group consisting of aryl, substituted aryl, heteroaryl, and substituted heteroaryl;

$R_6$ is selected from the group consisting of —$CR_7R_8CR_9R_{10}(CR_{11}R_{12})_nR_{13}$ and

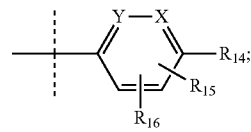

$R_7$, $R_8$, $R_9$, $R_{10}$, $R_{11}$, and $R_{12}$ are each independently selected from the group consisting of hydrogen, hydroxyl, halogen, $C_1$-$C_6$ alkyl, $C_3$-$C_6$ cycloalkyl, aryl, substituted aryl, heteroaryl, substituted heteroaryl and wherein $R_9$ and $R_{10}$ together form a $C_3$-$C_6$ cycloalkyl;

$R_{13}$ is selected from the group consisting of COOH and $NH_2SO_2CF_3$;

$R_{14}$ is selected from the group consisting of OH, COOH, and $SO_2NH_2$;

$R_{15}$ and $R_{16}$ are independently selected from the group consisting of hydrogen, hydroxyl, carboxyl, $NO_2$, and halogen;

n is 0 or 1; and

X and Y are independently selected from the group consisting of C and N.

2. The compound of claim 1 wherein $R_5$ is selected from the group consisting of 4-chlorophenyl, 3-chlorophenyl, 4-chloro-2-methoxyphenyl, 4-bromophenyl, 3-bromophenyl, 4-fluorophenyl, 3-fluorophenyl, 4-hydroxyphenyl, 4-methoxyphenyl, 3-methoxyphenyl, 2-methoxyphenyl, 4-chlorothiophen-2-yl, 5-chlorothiophen-2-yl, 3-bromothiophen-2-yl, 4-bromothiophen-2-yl, 5-bromothiopheny-2-yl, 5-bromothiophen-3-yl,

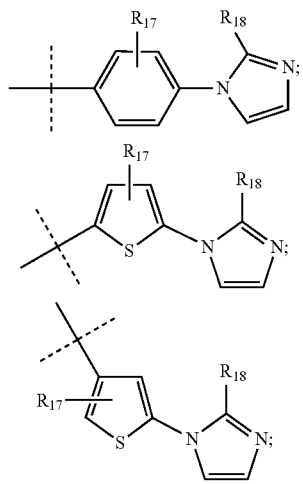

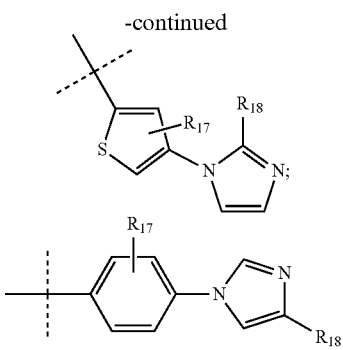

wherein
R$_{17}$ is selected from the group consisting of hydrogen, methyl, chloro, fluoro, hydroxy, methoxy, ethoxy, propoxy, carbamoyl, dimethylamino, amino, formamido, and trifluoromethyl; and
R$_{18}$ is selected from the group consisting of hydrogen, methyl, and ethyl.

3. The compound of claim 2 wherein R$_2$ is C$_1$-C$_6$ alkyl, R$_3$ is carbamoyl, and R$_4$ is hydrogen.

4. The compound of claim 3 wherein R$_5$ is selected from the group consisting of 4-methoxyphenyl, 4-chloro-2-methoxyphenyl, 4-(1H-imidazol-1-yl)phenyl, and 4-(2-methyl-1H-imidazol-1-yl)phenyl.

5. The compound of claim 1 selected from the group consisting of
3-(2-(4-carbamoyl-2-methylphenyl)-3-(4-methoxyphenyl)-1H-pyrrol-1-yl)propanoic acid;
3-(2-(4-carbamoyl-2-methylphenyl)-3-(4-methoxyphenyl)-1H-pyrrol-1-yl)-3-phenylpropanoic acid;
3-(2-(4-carbamoyl-2-methylphenyl)-3-(4-methoxyphenyl)-1H-pyrrol-1-yl)-2-methylpropanoic acid;
4-(2-(4-carbamoyl-2-methylphenyl)-3-(4-methoxyphenyl)-1H-pyrrol-1-yl)butanoic acid;
3-(3-(4-(1H-imidazol-1-yl)phenyl)-2-(4-carbamoyl-2-methylphenyl)-1H-pyrrol-1-yl)propanoic acid;
3-(2-(4-carbamoyl-2-methylphenyl)-1-(4-methoxyphenyl)-1H-pyrrol-3-yl)propanoic acid;
3-(2-(4-carbamoyl-2-methylphenyl)-3-(4-methoxyphenyl)-1H-pyrrol-1-yl)butanoic acid;
1-((2-(4-carbamoyl-2-methylphenyl)-3-(4-methoxyphenyl)-1H-pyrrol-1-yl)methyl)cyclopropanecarboxylic acid;
3-(2-(4-carbamoyl-2-methylphenyl)-3-(4-methoxyphenyl)-1H-pyrrol-1-yl)-2,2-difluoropropanoic acid;
3-(2-(4-carbamoyl-2-methylphenyl)-3-(4-methoxyphenyl)-1H-pyrrol-1-yl)-2-hydroxypropanoic acid;
3-(2-(4-carbamoyl-2-methylphenyl)-3-(4-methoxyphenyl)-1H-pyrrol-1-yl)hexanoic acid;
3-(2-(4-carbamoyl-2-methylphenyl)-3-(4-methoxyphenyl)-1H-pyrrol-1-yl)-4-methylpentanoic acid;
3-(1-(4-(1H-imidazol-1-yl)phenyl)-2-(4-carbamoyl-2-methylphenyl)-1H-pyrrol-3-yl)propanoic acid;
3-(2-(4-carbamoyl-2-methylphenyl)-1-(4-chloro-2-methoxyphenyl)-1H-pyrrol-3-yl)propanoic acid;
4-(2-(4-carbamoyl-2-methylphenyl)-3-(4-methoxyphenyl)-1H-pyrrol-1-yl)-2-hydroxybenzoic acid;
4-(2-(4-carbamoyl-2-methylphenyl)-3-(4-methoxyphenyl)-1H-pyrrol-1-yl)-2-fluorobenzoic acid;
4-(1-(4-hydroxy-3-nitrophenyl)-3-(4-methoxyphenyl)-1H-pyrrol-2-yl)-3-methylbenzamide;
4-(1-(6-hydroxypyridin-3-yl)-3-(4-methoxyphenyl)-1H-pyrrol-2-yl)-3-methylbenzamide;
4-(2-(4-carbamoyl-2-methylphenyl)-3-(4-methoxyphenyl)-1H-pyrrol-1-yl)benzoic acid;
4-(2-(4-carbamoyl-2-methylphenyl)-3-(4-methoxyphenyl)-1H-pyrrol-1-yl)-2-chlorobenzoic acid;
4-(3-(4-methoxyphenyl)-1-(2-(trifluoromethylsulfonamido)ethyl)-1H-pyrrol-2-yl)-3-methylbenzamide;
4-(3-(4-methoxyphenyl)- 1- (4-sulfamoylphenyl)-1H-pyrrol-2-yl)-3-methylbenzamide;
4-(1 -(3-fluoro-4-hydroxyphenyl)-3-(4-methoxyphenyl)-1H-pyrrol-2-yl)-3-methylbenzamide;
5-(2-(4-carbamoyl-2-methylphenyl)-3-(4-methoxyphenyl)-1H-pyrrol- 1 -yl)picolinic acid;
4-(1-(3,5-difluoro-4-hydroxyphenyl)-3-(4-methoxyphenyl) -1H-pyrrol-2-yl)-3-methylbenzamide;
4-(1-(5-hydroxypyridin-2-yl)-3-(4-methoxyphenyl)-1H-pyrrol-2-yl)-3-methylbenzamide;
5-(2-(4-carbamoyl-2-methylphenyl)-3-(4-methoxyphenyl)-1H-pyrrol-1-yl)-2-hydroxybenzoic acid;
6-(2-(4-carbamoyl-2-methylphenyl)-3-(4-methoxyphenyl)-1H-pyrrol-1-yl)nicotinic acid;
4-(1-(3-fluoro-4-hydroxyphenyl)-3-(4-(2-methyl-1H-imidazol-1-yl)phenyl)-1H-pyrrol-2-yl) -3-methylbenzamide; and
4-(3,5-difluoro-4-hydroxyphenyl)-3-(4-(2-methyl-1H -imidazol-1 -yl)phenyl)-1H-pyrrol-2-yl)-3-methylbenzamide.

6. A pharmaceutical composition comprising a therapeutically effective amount of a compound according to claim 1 together with a pharmaceutically accepted carrier or excipient.

7. A method of treatment of a pulmonary disorder which comprises administering a therapeutically effective amount of a compound of formula I as defined in claim 1 to a patient in need thereof.

8. The method of claim 7, wherein said pulmonary disorder is selected from the group consisting of asthma, cystic fibrosis and COPD.

* * * * *